(12) United States Patent
Yamashita

(10) Patent No.: US 11,445,999 B2
(45) Date of Patent: Sep. 20, 2022

(54) MEDICAL DEVICE

(71) Applicant: TERUMO KABUSHIKI KAISHA, Tokyo (JP)

(72) Inventor: Yasunori Yamashita, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1164 days.

(21) Appl. No.: 15/644,572

(22) Filed: Jul. 7, 2017

(65) Prior Publication Data
US 2017/0303890 A1 Oct. 26, 2017

Related U.S. Application Data

(63) Continuation of application No. PCT/JP2016/050138, filed on Jan. 5, 2016.

(30) Foreign Application Priority Data

Jan. 7, 2015 (JP) .............................. JP2015-001318

(51) Int. Cl.
*A61B 8/12* (2006.01)
*A61B 8/13* (2006.01)
(Continued)

(52) U.S. Cl.
CPC .................. *A61B 8/12* (2013.01); *A61B 8/13* (2013.01); *A61B 8/445* (2013.01); *A61B 8/481* (2013.01);
(Continued)

(58) Field of Classification Search
None
See application file for complete search history.

(56) References Cited

U.S. PATENT DOCUMENTS 5,024,234 A * 6/1991 Leary .................. A61B 8/12
600/467
5,203,338 A 4/1993 Jang
(Continued)

FOREIGN PATENT DOCUMENTS

JP 08-503629 A 4/1996
JP 3367666 B2 1/2003
(Continued)

OTHER PUBLICATIONS

International Search Report (PCT/ISA/210) dated Mar. 1, 2016, by the Japanese Patent Office as the International Searching Authority for International Application No. PCT/JP2016/050138.
(Continued)

*Primary Examiner* — Katherine L Fernandez
*Assistant Examiner* — Michael S Kellogg
(74) *Attorney, Agent, or Firm* — Buchanan Ingersoll & Rooney PC

(57) ABSTRACT

An imaging medical device includes a shaft main body portion having an image acquiring lumen and a guide wire lumen. The shaft main body portion includes a first shaft proximal portion in which the image acquiring lumen is disposed, and a second shaft proximal portion in which the guide wire lumen is disposed, with the two being bifurcated. First and second hub portions are interlocked with the first and second shaft proximal portions respectively, and a transducer unit is fixed to a drive shaft. Reference line X represents the axis line of the shaft main body portion, θ1 represents the inclination of the central axis of the first hub portion relative to the reference line, θ2 represents the inclination of the central axis of the second hub portion relative to the reference line, and the relationship of |θ1|>|θ2| is satisfied.

19 Claims, 11 Drawing Sheets

(51) Int. Cl.
  *A61B 8/00* (2006.01)
  *A61B 8/08* (2006.01)
  *A61M 25/00* (2006.01)
  *A61M 25/09* (2006.01)
  *B29C 55/22* (2006.01)
  *B29C 65/02* (2006.01)
  *B29C 65/56* (2006.01)
  *B29C 65/00* (2006.01)
  *B29L 31/00* (2006.01)

(52) U.S. Cl.
  CPC .... *A61M 25/0009* (2013.01); *A61M 25/0041* (2013.01); *A61M 25/0097* (2013.01); *A61M 25/09041* (2013.01); *B29C 55/22* (2013.01); *B29C 65/02* (2013.01); *B29C 65/56* (2013.01); *B29C 66/5227* (2013.01); *A61M 2025/0018* (2013.01); *B29L 2031/753* (2013.01)

(56) References Cited

U.S. PATENT DOCUMENTS

| | | | |
|---|---|---|---|
| 5,314,408 A | 5/1994 | Salmon et al. | |
| 5,458,584 A | 10/1995 | Ginn et al. | |
| 5,976,093 A | 11/1999 | Jang | |
| 5,997,523 A | 12/1999 | Jang | |
| 6,234,971 B1 | 5/2001 | Jang | |
| 10,842,465 B2 | 11/2020 | Yamashita | |
| 2003/0036729 A1 | 2/2003 | Jang | |
| 2009/0264865 A1 | 10/2009 | Kawai | |
| 2011/0077463 A1 | 3/2011 | Hirota | |
| 2015/0088100 A1* | 3/2015 | Oborn | A61M 25/02 604/523 |
| 2017/0303891 A1 | 10/2017 | Yamashita | |

FOREIGN PATENT DOCUMENTS

| | | |
|---|---|---|
| JP | 2008-142351 A | 6/2008 |
| JP | 2011-072401 A | 4/2011 |
| JP | 2012-106099 A | 6/2012 |
| WO | WO 92/11055 A1 | 7/1992 |
| WO | WO 94/11038 A1 | 5/1994 |

OTHER PUBLICATIONS

Written Opinion (PCT/ISA/237) dated Mar. 1, 2016, by the Japanese Patent Office as the International Searching Authority for International Application No. PCT/JP2016/050138.

* cited by examiner

MEDICAL DEVICE

CROSS-REFERENCES TO RELATED APPLICATIONS

This application is a continuation of International Application No. PCT/JP2016/050138 filed on Jan. 5, 2016, and claims priority to Japanese Application No. 2015-001318 filed on Jan. 7, 2015, the entire content of both of which is incorporated herein by reference.

TECHNICAL FIELD

The present invention generally relates to a medical device insertable into a body lumen and configured to acquire image information.

BACKGROUND ART

When a target lesion in a lumen of a blood vessel, a vessel, and the like, is examined, an ultrasound catheter that transmits and receives ultrasound waves to and from the target lesion is used. The ultrasound catheter includes an imaging core that is provided with a transducer unit for transmitting and receiving the ultrasound waves and a drive shaft that causes the transducer unit to rotate, and a shaft portion in which the imaging core is internally installed and which is inserted in the lumen. The imaging core is movable in an axial direction of the shaft portion while rotating in the shaft portion.

For example, Japanese Application No. 8-503629 discloses an ultrasound catheter in which a lumen for images through which a work element for imaging is movable and a guide wire lumen in which a guide wire is accommodatable are formed on a proximal side, and an image acquiring lumen and the guide wire lumen converge in a common lumen on a distal side. In the ultrasound catheter, the work element for imaging is capable of reciprocating through the lumen for images on the proximal side and the common lumen on the distal side, and the guide wire is movable through the guide wire lumen on the proximal side and the common lumen on the distal side. The ultrasound catheter employs an over-the-wire structure in which the guide wire lumen extends to the vicinity of a proximal housing that is operated by an operator. The ultrasound catheter is an over-the-wire type, thereby being flexibly compliable with the guide wire used and being capable of efficiently transmitting a pushing force of the operator such that it is possible to acquire an image of a deep portion of a more complex region such as a bifurcated portion or a stenosed site of a blood vessel.

SUMMARY

In the ultrasound catheter disclosed in Japanese Application No. 8-503629, the guide wire lumen does not extend to the proximal housing that is operated by the operator, but is opened on the distal side from the proximal housing. Therefore, since it is possible for an opening portion of the guide wire lumen on the proximal side to approach a sheath for percutaneouly introducing the ultrasound catheter into the blood vessel, the opening portion is likely to be wetted with blood leaking from the sheath. Therefore, it is difficult to perform an interchange of the guide wire or an injection operation of a contrast agent, medicine, or the like via the guide wire lumen.

However, although the opening portion of the guide wire lumen on the proximal side is disposed in a hand-side portion, an external drive device for driving the work element is connected to the hand-side portion of the guide wire lumen, and thus motion of the external drive device and the operation of the guide wire interfere with each other and high operability is not obtained.

The medical device disclosed here addresses such problems described above, and is configured to exhibit high operability and acquire image information while employing an over-the-wire structure.

A medical device insertable into a body lumen to perform treatment comprises: a shaft main body portion formed as a double-lumen structure comprised of an instrument lumen for receiving a medical instrument and a guide wire lumen for receiving a guide wire, with the shaft main body portion possessing a distal end and a proximal end, and both the instrument lumen and the guide wire lumen extending from the distal side of the shaft main body portion to the proximal end of the shaft main body portion. A proximal portion of the shaft main body portion adjacent the proximal end of the shaft main body portion comprises a first shaft proximal portion in which a portion of the instrument lumen is disposed, and a second shaft proximal portion in which a portion of the guide wire lumen is disposed, with the first shaft proximal portion and the second shaft proximal portion being bifurcated. A shaft distal portion positioned distal of the shaft main body portion includes a common lumen structure into which the instrument lumen and the guide wire lumen converge. A hub is comprised of a first hub portion interlocked with the first shaft proximal portion and a second hub portion interlocked with the second shaft proximal portion, with the first hub portion possessing a central axis and the second hub portion possessing a central axis different from the central axis of the first hub portion. A drive shaft is positionable in the instrument lumen to be movable in both a rotating direction and an axial direction in the instrument lumen, a treatment unit is fixed to a distal end of the drive shaft and is configured to perform treatment, and an axis line of the shaft main body portion is a reference line, with θ1 representing an angle of inclination of the central axis of the first hub portion with respect to the reference line, and θ2 representing an angle of inclination of the central axis of the second hub portion with respect to the reference line, wherein the relationship of |θ1|>|θ2| is satisfied.

According to another aspect, an image-acquiring medical device insertable into a body lumen to acquire images inside the body lumen comprises: a shaft main body portion possessing a distal end at one end of the shaft main body portion and a proximal end at an opposite end of the shaft main body portion, with the shaft main body including two lumens extending throughout a length of the shaft main body portion from the distal end of the shaft main body portion to the proximal end of the shaft main body portion, and wherein the two lumens of the shaft main body are separated from one another along the length of the shaft main body portion by a wall, and the two lumens in the shaft main body comprise an image acquiring lumen for acquiring images and a guide wire lumen for receiving a guide wire. A proximal portion of the shaft main body includes a first shaft proximal portion, in which a portion of the image acquiring is disposed, and a second shaft proximal portion, in which a portion of the guide wire lumen is disposed, with the first shaft proximal portion and the second shaft proximal portion being bifurcated. A shaft distal portion is connected to the distal end of the shaft main body, and the shaft distal portion possesses an open distal end and an open proximal end, with the shaft distal portion including a lumen that extends from the open proximal end of the shaft distal portion to the open distal end of the shaft distal portion. The open proximal end of the shaft main body communicates with both the guide wire lumen and the image acquiring lumen so that a guide wire is guidable along the lumen in the shaft main body and along the lumen in the shaft distal portion while extending distally beyond the open distal end of the shaft distal portion and proximally beyond a proximal end of the second shaft proximal portion. A hub includes a first hub portion interlocked with the first shaft proximal portion and a second hub portion interlocked with the second shaft proximal portion, and the first hub portion and the second hub portion each possess a central axis. A drive shaft is rotatably positioned in the image acquiring lumen and is axially movable in the image acquiring lumen. An image acquiring unit is configured to acquire images and is fixed to the distal end of the drive shaft so that axial and rotational movement of the drive shaft results in axial and rotational movement respectively of the image acquiring unit. The shaft main body portion possesses an axis line constituting a reference line, an inclination of the central axis of the first hub portion with respect to the reference line being represented by an angle θ1, an inclination of the central axis of the second hub portion with respect to the reference line being represented by θ2, and a relationship of |θ1|>|θ2θ is satisfied.

In the medical device having such a configuration, since the first hub portion and the second hub portion face in different directions from each other, motion of an imaging unit via the image acquiring lumen and an operation of the guide wire via the guide wire lumen do not interfere with each other, and thus it is possible to exhibit high operability, even in an over-the-wire structure in which opening portions of the guide wire lumen and the image acquiring lumen on the proximal side are formed in the same hub. Further, the relationship of |θ1|>|θ2θ is satisfied, and thereby it is possible to normally maintain the operability of the guide wire having rigidity higher than that of the drive shaft, to the highest extent.

The hub may further be provided with a hub casing that collectively covers the first shaft proximal portion, the second shaft proximal portion, the first hub portion, and the second hub portion. In this manner, the drive shaft is held in the first shaft proximal portion in the hub casing, and thus the drive shaft is unlikely to have distortion or sliding failure such that it is possible to acquire good images. Further, the guide wire is held in the second shaft proximal portion inside the hub casing, and thus the guide wire is unlikely to have distortion or sliding failure inside the hub casing such that it is possible to achieve a good operation of the guide wire.

The hub casing is configured to have a split type structure so as to interpose outer peripheral surfaces of the first hub portion and the second hub portion from both sides, and thus it is possible to easily dispose, inside the hub casing, the first hub portion and the second hub portion, which are inclined in different directions. Since it is possible to easily dispose the first hub portion, the second hub portion, and the shaft main body portion inside the hub casing, it is possible to reliably hold a bifurcated region of the proximal portion of the shaft main body portion inside the hub casing. Therefore, a bifurcated portion of the shaft main body portion, which has low rigidity, is not positioned on the distal side from the hub casing. In this manner, the shaft main body portion can exhibit high pushing performance, thus it is possible to reduce an occurrence of a kink, and it is possible to reduce an occurrence of attachment or the like of thrombus in a recessed portion of the bifurcated portion.

A direction of the inclination of the central axis of the first hub portion with respect to the reference line may be an opposite direction to a direction of the inclination of the central axis of the second hub portion with respect to the reference line. In this manner, an angle between the drive shaft and the guide wire increases while bending of the drive shaft and the guide wire is reduced as much as possible, and thus it is possible to reduce an occurrence of interference of motion of the imaging unit via the image acquiring lumen with the operation of the guide wire via the guide wire lumen, as much as possible.

According to another aspect, a method of fabricating a medical device comprises: linearly stretching a first tube made of plastic material to produce a stretched first tube; and heating a portion of the stretched first tube as well as a portion of a second plastic tube positioned adjacent the stretched first tube while pressing the portion of the stretched first tube and the portion of the second plastic tube against each other to heat-welded the portion of the stretched first tube and the portion of the second plastic tube to one another to integrate the portion of the stretched first tube and the portion of the second plastic tube to thereby produce a shaft main body portion. The heating of the portion of the stretched first tube as well as the portion of a second plastic tube also includes not heating a proximal portion of the stretched first tube and not heating a proximal portion of the second plastic tube so that the proximal portion of the stretched first tube is not heat-welded to the proximal portion of the second plastic tube. The method also includes interlocking a first hub portion to the proximal portion of the stretched first tube in an airtight manner, and interlocking a second hub portion with the proximal portion of the second plastic tube, with the first hub portion possessing a central axis and the second hub portion possessing a central axis different from the central axis of the first hub portion. The method additionally involves covering the first hub and the second hub portion with a hub casing so that an axis line of the shaft main body portion is a reference line, θ1 represents an angle of inclination of the central axis of the first hub portion with respect to the reference line and θ2 represents an angle of inclination of the central axis of the second hub portion with respect to the reference line, and a relationship of |θ1|>|θ2θ is satisfied.

DETAILED DESCRIPTION

Figure 1:
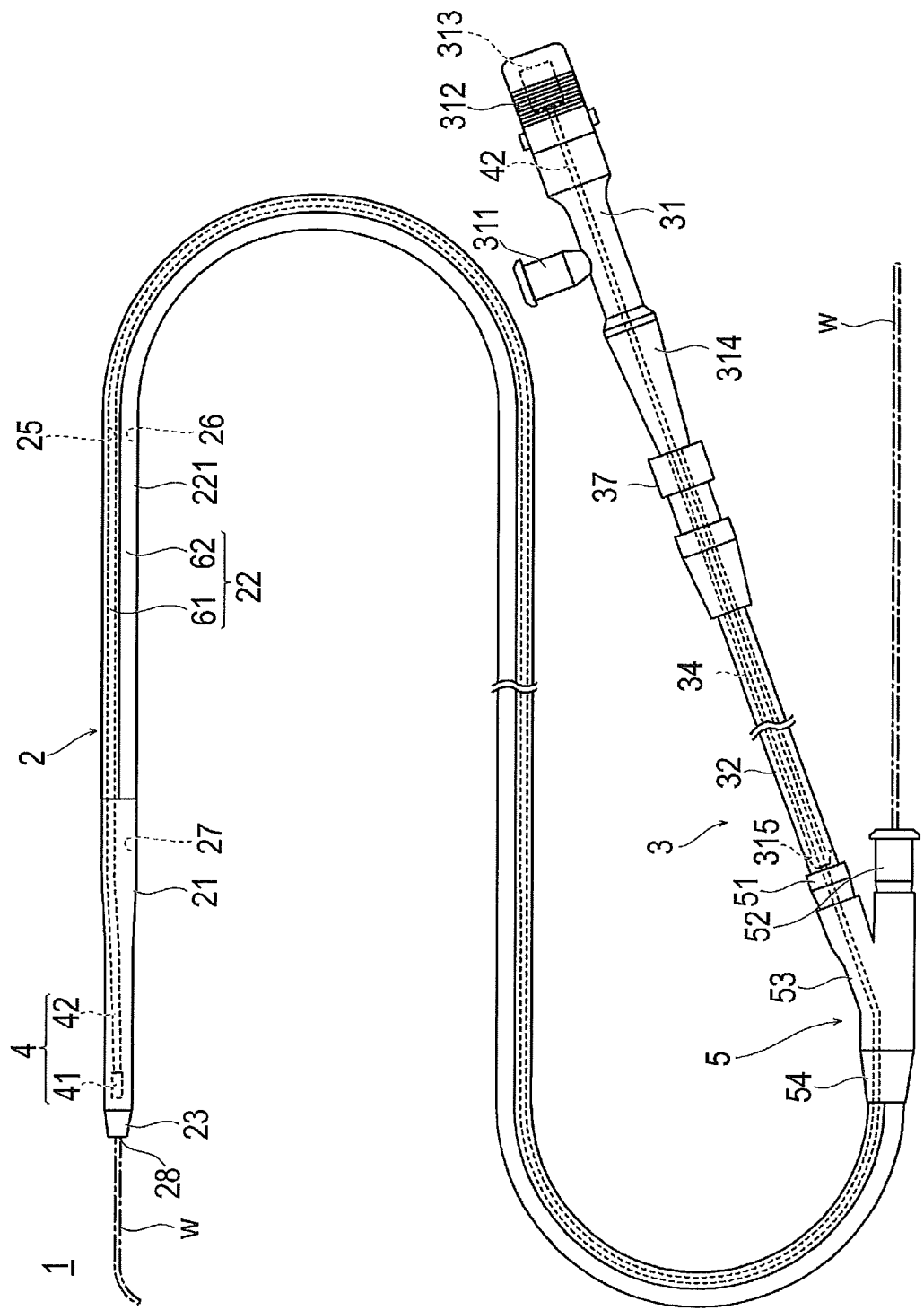
FIG. 1 is a plan view illustrating a medical device according to an embodiment.

Set forth below with reference to the accompanying drawing figures is a detailed description of an embodiment of a medical device representing one example of the inventive medical device disclosed here. A dimension ratio in the figures is enlarged depending on the description and the ratio is different from an actual ratio in some cases.

As illustrated in FIGS. 1 to 4, a medical device 1 is an ultrasound catheter that accommodates an imaging core 4 for performing ultrasound diagnosis and is configured to be inserted into a body lumen. The medical device 1 is connected to an external drive device 7 (refer to FIG. 8) that holds the medical device 1 and drives the imaging core 4, and the medical device is mainly used for performing diagnosis in a blood vessel. In this specification, a side, on which insertion into a lumen of a living body is performed, is referred to as a "distal end" or a "distal side", and a hand side, on which an operation is performed, is referred to as a "proximal end" or a "proximal side".

The medical device 1 includes a shaft portion 2 that is inserted into the lumen in the living body, the imaging core 4 (imaging unit) that transmits and receives ultrasound waves toward and from tissue in a lumen, a hub 5 through which the imaging core 4 penetrates and which is positioned on the proximal side from a shaft portion 2, and an operation unit 3 that operates the imaging core 4.

The shaft portion 2 includes a shaft distal portion 21, a shaft main body portion 22 that is disposed on the proximal side of the shaft distal portion 21, and a distal tip 23 that is disposed on the distal side of the shaft distal portion 21.

Figure 2:
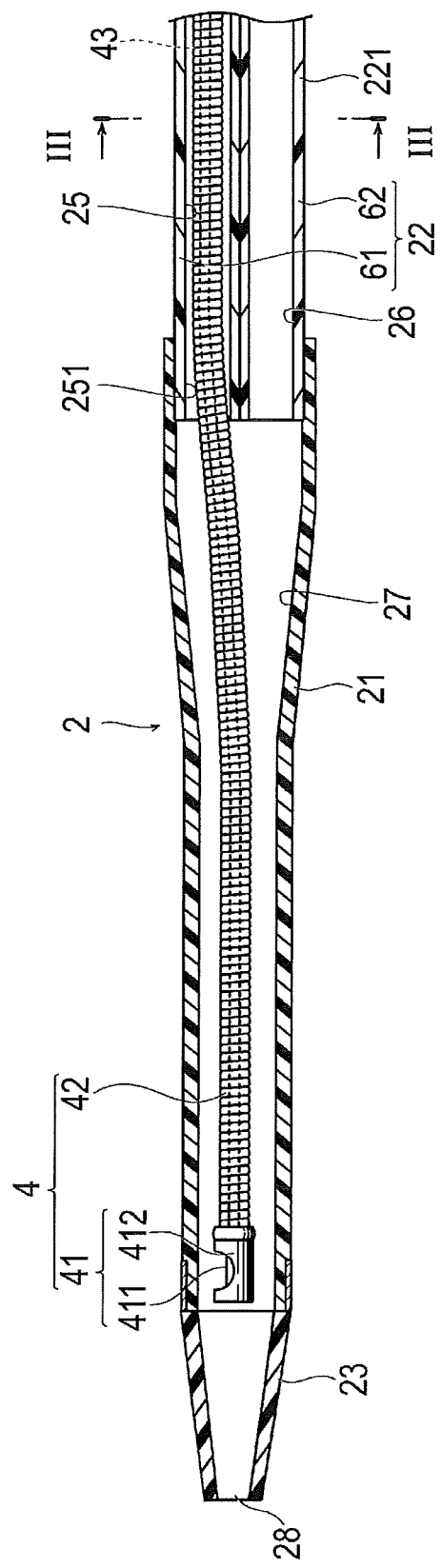
FIG. 2 is a longitudinal-sectional view illustrating a distal portion of the medical device according to the embodiment.
Figure 3:
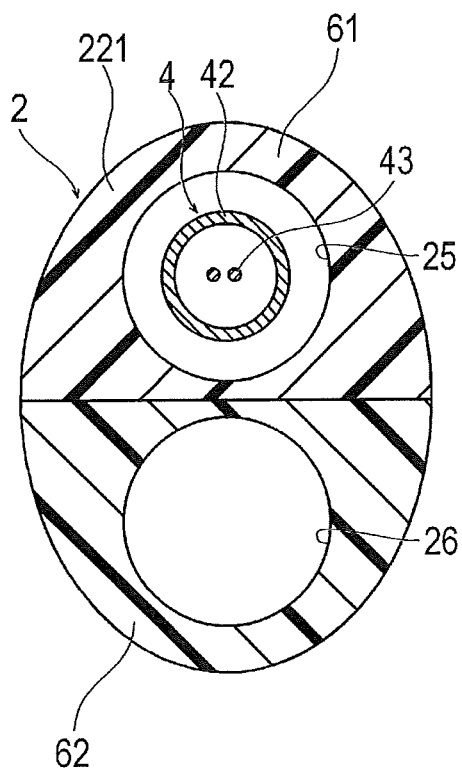
FIG. 3 is a cross-sectional view taken along the section line III-III in FIG. 2.

The shaft main body portion 22 is provided with an image acquiring lumen or instrument lumen 25 into which the imaging core or medical instrument 4 is inserted or positioned and a guide wire lumen 26 into which a guide wire W is inserted or positioned. The image acquiring lumen 25 and the guide wire lumen 26 are separated by a wall as shown in FIG. 2 and are formed to penetrate from the distal side to the proximal side of the shaft main body portion 22. That is, the image acquiring lumen 25 and the guide wire lumen 26 both pass completely through the shaft main body portion 22 from the distal end to the proximal end. The shaft main body portion 22 is provided with an intermediate shaft portion 221 in which the image acquiring lumen 25 and the guide wire lumen 26 are parallel to each other on the distal side, and a first shaft proximal portion 222 and a second shaft proximal portion 223 which are bifurcated and extend from the intermediate shaft portion 221 in a proximal direction. The image acquiring lumen 25 is formed or positioned inside the first shaft proximal portion 222, and the guide wire lumen 26 is formed or positioned inside the second shaft proximal portion 223. The shaft main body portion 22 may have an outer diameter and an inner diameter which are different depending on a position in an axial direction. For example, the outer diameter and the inner diameter may decrease to have a tapered shape from the proximal side to the distal side such that physical properties do not remarkably change, and thereby it is possible to reduce an occurrence of a kink while high pushing performance and passability are realized.

The shaft main body portion 22 is formed by or comprised of a first pipe body 61 in which the image acquiring lumen 25 is formed, and a second pipe body 62 in which the guide wire lumen 26 is formed. The first pipe body 61 and the second pipe body 62 are positioned side-by-side, are connected by heat-welding (or adhesion), have colors different from each other (i.e., the first pipe body 61 is of a different and visually distinguishable color relative to the color of the second pipe body 62), and have transparency allowing the inside of the first and second pipe bodies 61, 62 to be observed. In this manner, while observing the inside of the shaft portion 2, it is possible to insert the guide wire W not into the image acquiring lumen 25, but selectively into the guide wire lumen 26.

The shaft distal portion 21 is provided with one common lumen 27 (also called a single lumen), in which the image acquiring lumen 25 and the guide wire lumen 26 converge or communicate. The shaft distal portion 21 is open at both ends (the proximal and distal ends). Hence, it is possible for the guide wire W from the guide wire lumen 26 and the imaging core 4 from the image acquiring lumen 25 to enter the common lumen 27.

The distal tip 23 is a pipe body that is made of a flexible material, is disposed on the distal side of the shaft distal portion 21, and is provided with a distal opening portion 28 which communicates with the common lumen 27. The distal tip 23 reduces an impact on biological tissue brought into contact with the tip when the medical device 1 moves inside the body lumen.

The imaging core 4 is slidably disposed in the image acquiring lumen 25 in the axial direction of the shaft portion 2. The imaging core 4 is provided with a transducer unit 41 for transmitting and receiving the ultrasound waves to and from biological tissue from the lumen, and a drive shaft 42 having a distal end at which is attached the transducer unit 41 so that the drive shaft 42 is able to cause the transducer unit to rotate. The transducer unit 41 is configured to include an ultrasound transducer 411 that transmits and receives the ultrasound waves, and a housing 412 that accommodates the ultrasound transducer 411.

The shaft distal portion 21 is made of a material having high transmittivity of the ultrasound waves. The shaft distal portion 21 is made of a material having flexibility, and there is no particular limitation on the material. Examples of the material include various types of plastic elastomers such as styrene-based elastomer, polyolefin-based elastomer, polyurethane-based elastomer, polyester-based elastomer, polyamide-based elastomer, polyimide-based elastomer, polybutadiene-based elastomer, trans-polyisoprene-based elastomer, fluororubber-based elastomer, or chlorinated polyethylene-based elastomer, and it is possible to apply a combination (a polymer alloy, a polymer blend, a laminated body, or the like) of one or more types thereof.

The shaft main body portion 22 is made of a material having flexibility, and there is no particular limitation on the material. For example, it is possible to apply the materials that can be applied to the shaft distal portion 21 described above.

The distal tip 23 is made of a material that is more flexible than that of the shaft distal portion 21, and there is no particular limitation on the material. For example, it is possible to apply the materials that can be applied to the shaft distal portion 21 described above.

The drive shaft 42 is flexible and has characteristics of being capable of transmitting power of rotation generated in the operation unit 3 to the transducer unit 41. For example, the drive shaft is configured of a pipe body having a multi-layer coil shape such as a three-layer coil formed to have winding directions of rightward, leftward, and rightward direction alternately in the radial direction so that adjacent windings are wound in the opposite direction. The drive shaft 42 transmits the power of rotation, thereby the transducer unit 41 rotates, and it is possible to observe a target lesion in a lumen of a blood vessel or the like in a circumferential direction. In addition, a signal line 43 for transferring a signal detected by the transducer unit 41 to the operation unit 3 passes through the inside of the drive shaft 42.

The hub 5 is provided with a first hub portion 51 that is interlocked with the first shaft proximal portion 222 in an airtight manner, a second hub portion 52 that is interlocked with the second shaft proximal portion 223 in an airtight manner, a hub casing 53 that covers the first hub portion 51 and the second hub portion 52, and a first anti-kink protector 54.

The operation unit 3 that is interlocked with the external drive device 7 in order to operate the imaging core 4 is interlocked with the first hub portion 51. The operation unit 3 is provided with an outer tube 32 that is interlocked with the first hub portion 51, a unit connector 37 that is interlocked with a proximal portion of the outer tube 32, an inner tube 34 that is movable in the axial direction with respect to the outer tube 32, and an operation proximal portion 31 that is interlocked with the proximal portion of the inner tube 34.

The operation proximal portion 31 holds the drive shaft 42 and the inner tube 34. The operation proximal portion 31 moves such that the inner tube 34 is pushed into the unit connector 37 and the outer tube 32 (refer to FIG. 1), or is pulled out (refer to FIG. 9), and the drive shaft 42 is coupled to the operation proximal portion 31 and slides in the shaft portion 2 in the axial direction. The operation proximal portion 31 is provided with a port 311 into which saline (saline solution) for priming is injected. The port 311 communicates with the image acquiring lumen 25.

As illustrated in FIG. 1, when the inner tube 34 is pushed to the greatest extent (i.e., moved to the greatest extent in the axial forward direction), the end portion of the inner tube 34 on the distal side moves inside the outer tube 32 and reaches the vicinity of the first hub portion 51. As illustrated in FIG. 2, in this state, the transducer unit 41 is positioned in the vicinity of the distal end of the common lumen 27 of the shaft portion 2.

Figure 9:
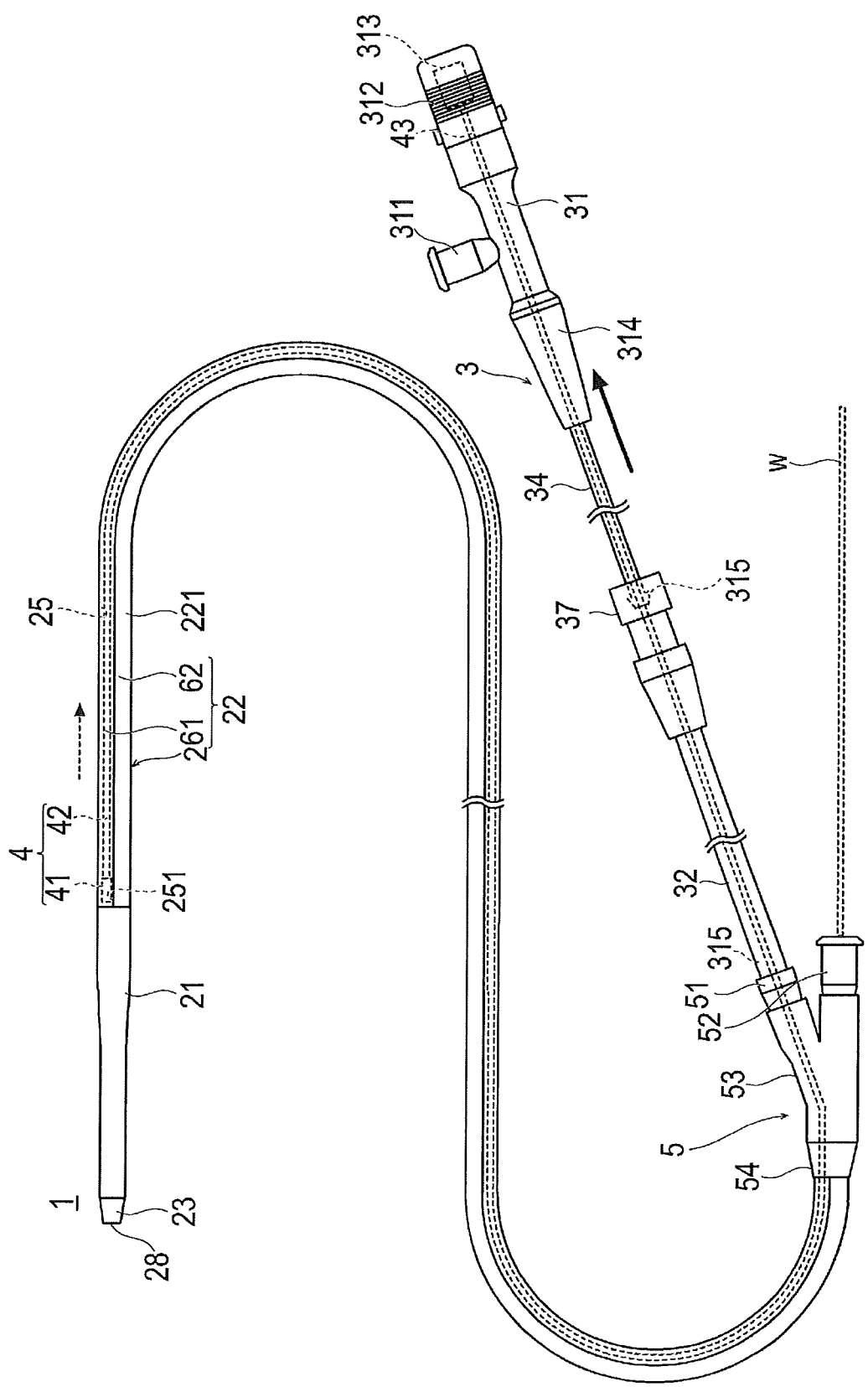
FIG. 9 is a plan view illustrating the medical device when a transducer unit is pulled back.

In addition, as illustrated in FIG. 9, when the inner tube 34 is pulled out to the greatest extent, a stopper 315 formed on the distal end of the inner tube 34 is clasped to an inner wall of the unit connector 37, and the inner tube except for the vicinity of the clasped distal end is exposed. In this state, the transducer unit 41 is pulled back through the inside of the shaft portion 2 while remaining in the shaft portion, and is accommodated in an accommodation unit 251 formed in a distal region of the image acquiring lumen 25. As described above, the transducer unit 41 is movable inside the common lumen 27 and the image acquiring lumen 25 in the axial direction while rotating so as to generate a tomographic image of a blood vessel or the like.

The operation proximal portion 31 includes a joint 312, a hub-side connector 313 connected to the proximal portion of the drive shaft 42, and a second anti-kink protector 314.

The joint 312 is provided with an opening portion on the proximal side of the joint 312, and the hub-side connector 313 is disposed inside the joint 312. The hub-side connector 313 can be interlocked with a drive-side connector 711 (refer to FIG. 8) provided in the external drive device 7 from the proximal side of the joint 312, and the interconnection causes the external drive device 7 and the hub-side connector 313 to be mechanically and electrically connected to each other.

As illustrated in FIG. 2, one end of the signal line 43 is connected to the hub-side connector 313, and the other end of the signal line 43 passes through the drive shaft 42 and is connected to the transducer unit 41. Irradiation with the ultrasound waves is performed from the transducer unit 41 in response to a signal transmitted from the external drive device 7 via the drive-side connector 711, the hub-side connector 313, and the signal line 43, to the transducer unit 41. In addition, a signal detected by the transducer unit 41 by receiving the ultrasound waves is transferred to the external drive device 7 via the signal line 43, the hub-side connector 313, and the drive-side connector 711.

The second anti-kink protector 314 is disposed on the periphery of the inner tube 34 and the operation proximal portion 31 and reduces kinking of the inner tube 34.

The outer tube 32 is fixed to the proximal end of the first hub portion that projects proximally beyond the proximal-most end of the hub casing 53. The outer tube 32 that is attached to the first hub portion 51 includes a proximal portion inserted to be fitted into the inside of, or positioned inside, the unit connector 37, and the inner tube 34 extending from the operation proximal portion 31 is inserted into or positioned inside the inside of the outer tube 32. The unit connector 37 can be connected to a holding portion 73 (refer to FIG. 8) of the external drive device 9.

Figure 4:
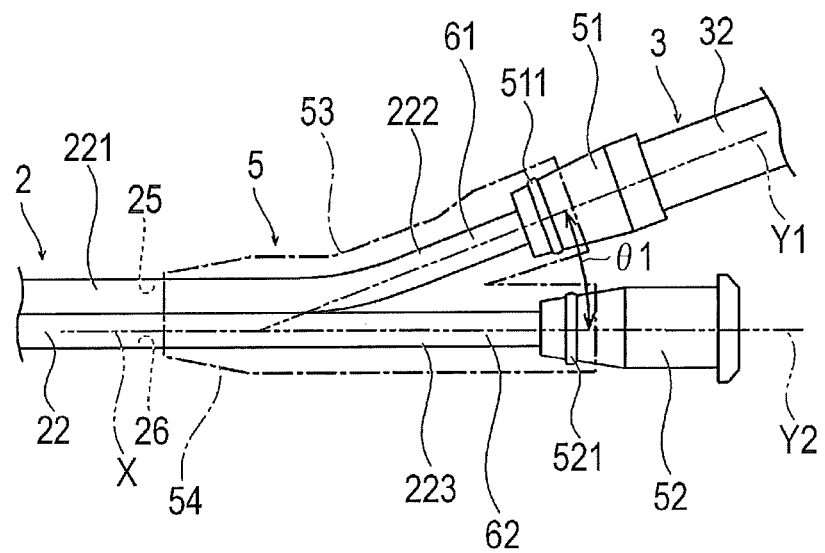
FIG. 4 is a plan view illustrating a hub of the medical device according to the embodiment.

As illustrated in FIGS. 1 and 4, the distal portion of the outer tube 32 is interlocked with the first hub portion 51 so that the distal portion of the outer tube 32 is fitted in the first hub portion 51 from the proximal side of the first hub portion 51, and the first shaft proximal portion 222 is inserted into (positioned in) and is interlocked with the first hub portion from the distal side of the first hub portion 51 through heat-welding or adhesion in an airtight manner. Hence, the drive shaft 42 and the saline passing through the inner tube 34 and the outer tube 32 are movable to the image acquiring lumen 25 through the first hub portion 51. That is, the outer tube 32, the first hub portion 51, the first shaft proximal portion 222 and the image acquiring lumen 25 communicate with each other so that the drive shaft 42 and saline can pass along such path. The first hub portion 51 is provided with a first interlocking convex portion 511 that projects outwardly to have a ring shape, on the outer peripheral surface of the first hub portion so as to be interlocked with the hub casing 53.

The second shaft proximal portion 223 is inserted into (positioned in) and is interlocked with the second hub portion 52 from the distal side of the second hub portion 52 through heat-welding or adhesion in an airtight manner. Hence, the second hub portion 52 communicates with the guide wire lumen 26 and the guide wire W can pass through the second hub portion. The second hub portion 52 is provided with a second interlocking convex portion 521 that projects outwardly to have a ring shape, on the outer peripheral surface of the second hub portion so as to be interlocked with the hub casing 53.

Figure 5:
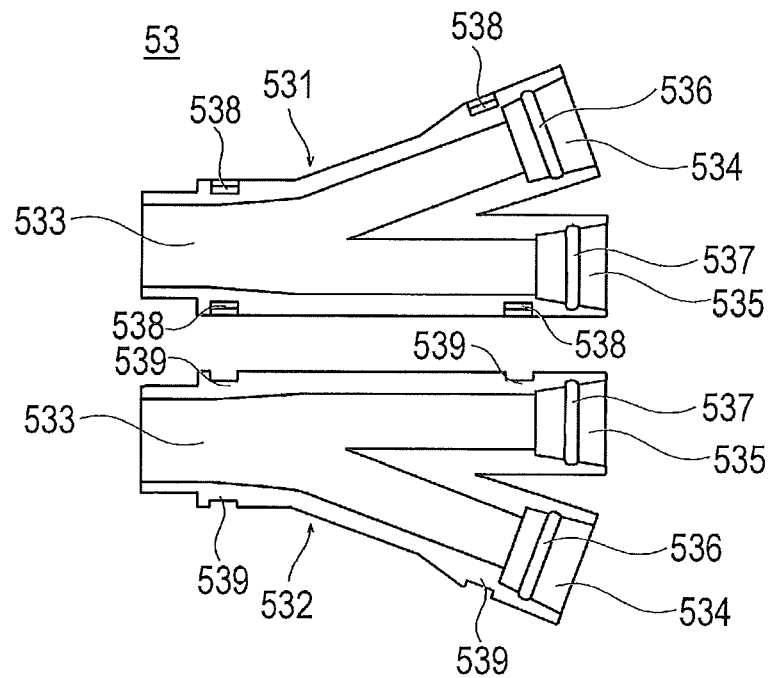
FIG. 5 is a plan view illustrating a first casing and a second casing.
Figure 6:
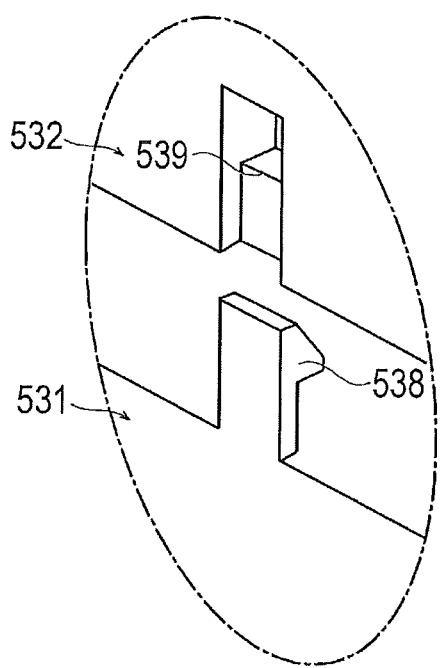
FIG. 6 is a perspective view illustrating parts of the first casing and the second casing in an enlarged manner.

As illustrated in FIGS. 4 to 6, the hub casing 53 includes two casings, namely a first casing 531 and a second casing 532 which have a split type structure so as to interpose outer peripheral surfaces of the shaft main body portion 22, the first hub portion 51, and the second hub portion 52 from both sides. That is, distal portions of the first and second hub portions 51, 52 and a proximal portion of the shaft main body portion 22 are positioned between the two casings 531, 532. The first casing 531 and the second casing 532 have a symmetrical shape so as to interpose the shaft main body portion 22, the first casing 531, and the second casing 532. The first casing 531 and the second casing 532 are provided with a distal side fitting portion 533 in which the shaft main body portion 22 is fitted, a first hub fitting portion 534 in which the first hub portion 51 is fitted, and a second hub fitting portion 535 in which the second hub portion 52 is fitted.

The first hub fitting portion 534 is provided with a first interlocking concave portion (recess) 536 in which the first interlocking convex portion (projection) 511 formed on the outer peripheral surface of the first hub portion 51 is fittable or positioned. The second hub fitting portion 535 is provided with a second interlocking concave portion (recess) 537 in which the second interlocking convex portion (projection) 521 formed on the outer peripheral surface of the second hub portion 52 is fittable or positioned.

The first casing 531 and the second casing 532 are provided with a first interlocking hook 538 and the second interlocking stepped portion 539 which are interlocked with each other so as to perform hooking (mechanical connection), by overlapping the outer peripheral surfaces of the shaft main body portion 22, the first hub portion 51, and the second hub portion 52 such that the outer peripheral surfaces are interposed from both sides. The first casing 531 and the second casing 532 overlap each other. In this manner, the interlocking hook 538 is temporarily bent and, then, is hooked into the interlocking stepped portion 539, and the first casing 531 and the second casing 532 are interlocked with each other. The first casing 531 and the second casing 532 may alternatively be bonded with an adhesive or through heat-welding without using a mechanical structure such as the interlocking hook 538 and the interlocking stepped portion 539.

When the first casing 531 and the second casing 532 are interlocked with each other in a state in which the first interlocking convex portion 511 of the first hub portion 51 is fitted in the first interlocking concave portion 536, and the second interlocking convex portion 521 of the second hub portion 52 is fitted in the second interlocking concave portion 537, the first hub portion 51 and the second hub portion 52 are fixed to the hub casing 53 so as not to be dropped off (i.e., the first hub portion 51 and the second hub portion 52 are fixed to the hub casing 53 so that the first and second hub portions 51, 52 do not become separated from the hub casing 53). The first hub portion 51 and the hub casing 53 may also be bonded with an adhesive or through heat-welding without using a mechanical structure such as the first interlocking convex portion 511 and the first interlocking concave portion 536. The second hub portion 52 and the hub casing 53 may also be bonded with an adhesive or through heat-welding without using a mechanical structure such as the second interlocking convex portion 521 and the second interlocking concave portion 537.

The shaft main body portion 22 is bifurcated into the first shaft proximal portion 222 and the second shaft proximal portion 223 from the intermediate shaft portion 221 in the proximal direction in a region which is positioned inside the hub casing 53. Therefore, the first pipe body 61 and the second pipe body 62 are not bonded to each other in this region, and thereby the first shaft proximal portion 222 and the second shaft proximal portion 223 having rigidity lower than that of the intermediate shaft portion 221 are not positioned out of the hub casing 53 and are capable of exhibiting high pushing performance. That is, it is possible to reliably hold the bifurcated region of the proximal portion of the shaft main body portion 22 inside the hub casing 53. Therefore, a bifurcated portion of the shaft main body portion 22, which has relatively low rigidity, is not positioned on the distal side from the hub casing 53 (i.e., does not project distally beyond the distal end of the hub casing). In this manner, the shaft main body portion 22 can exhibit high pushing performance, and so it is possible to reduce an occurrence of kinking, and it is also possible to reduce an occurrence of attachment or the like of thrombus in a recessed portion of the bifurcated portion.

In a case where, in the hub casing 53, with an axis line (central axis) X of the proximal portion of the shaft main body portion 22 as a reference line, θ1 represents the inclination of a central axis Y1 of the first hub portion 51 with respect to the reference line X, and θ2 represents the inclination of a central axis Y2 of the second hub portion 52 with respect to the reference line X, it is preferable that the following expression (1) is satisfied.

$$|θ1|>|θ2| \qquad \text{Expression (1)}$$

When the inclination |θ1| of the first hub portion 51 is significantly large, unevenness in rotation for an image is likely to occur due to friction between the drive shaft 42 and the first shaft proximal portion 222. In addition, when the imaging core 4 is pulled back, disconnection or unevenness in image is likely to occur due to jumping by disorder in the movement of the imaging core 4. Therefore, it is preferable that the inclination |θ1| is an angle selected so that the rotational unevenness, disconnection, jumping, or the like do not occur in the imaging core 4.

When the inclination |θ2| of the second hub portion 52 is significantly large, there is a possibility that operability of the guide wire W may be degraded due to friction between the guide wire W and the second shaft proximal portion 223.

Therefore, in consideration of such points described above, there may be a preference for |θ1|≈0, |θ2|≈0. That is, there may be a preference for the angle |θ1| to be nearly equal to zero and for the angle |θ2| to be nearly equal to zero. However, the smaller the number of the angular difference |θ1−θ2| between the central axis Y1 of the first hub portion 51 and the central axis Y2 of the hub portion 52, the further the operation of the guide wire W by an operator interferes with the external drive device 7. Hence, it is preferable that the value of |θ1−θ2| is as large as possible.

In addition, since the rigidity of the guide wire W is normally much higher than the rigidity of the drive shaft 42, preferably, |θ2|≈0. That is, the angle |θ2| should preferably be nearly zero. Taking into account these factors, in the disclosed embodiment of the medical device, |θ2|=0, and |θ1|>0.

The drive shaft is typically disposed so as not to be bent in the hub in general. But in the medical device here, the drive shaft 42 is disposed to be bent in the hub 5 in the embodiment. The drive shaft 42 is configured to transmit a drive force while being bent in the blood vessel, and thus it is possible to allow the drive shaft to be bent in the hub 5. Since the first shaft proximal portion 222, which is provided with the image acquiring lumen 25 that accommodates the drive shaft 42, extends in a bent configuration so as to be interlocked with the first hub portion 51 in the hub casing 53, it is possible to appropriately hold a position of the drive shaft 42 that rotates in the hub casing 53. In other words, if the drive shaft 42 extended within or is accommodated within a certain wide space in the hub casing 53 without being accommodated in the first shaft proximal portion 222, the drive shaft 42 may be distorted due to reciprocation of the drive shaft 42, and the distortion can result in sliding failure. However, in the described embodiment representing one example of the medical device disclosed here, since the drive shaft 42 is held by the first shaft proximal portion 222 in the hub casing 53, the distortion-sliding failure of the drive shaft 42 is unlikely to occur in the hub casing 53, and thus it is possible to acquire a good-quality image.

In addition, since the second shaft proximal portion 223, which is provided with the guide wire lumen 26 that accommodates the guide wire W, is interlocked with the second hub portion 52 in the hub casing 53, it is possible to appropriately hold a position of the guide wire W in the hub casing 53. Therefore, similar to the drive shaft 42 that is held in the aforementioned first shaft proximal portion 222 such that the distortion-sliding failure is unlikely to occur, distortion-sliding failure of the guide wire W is unlikely to occur in the hub casing 53, and thus it is possible to achieve a high-quality operation of the guide wire W.

Figure 7:
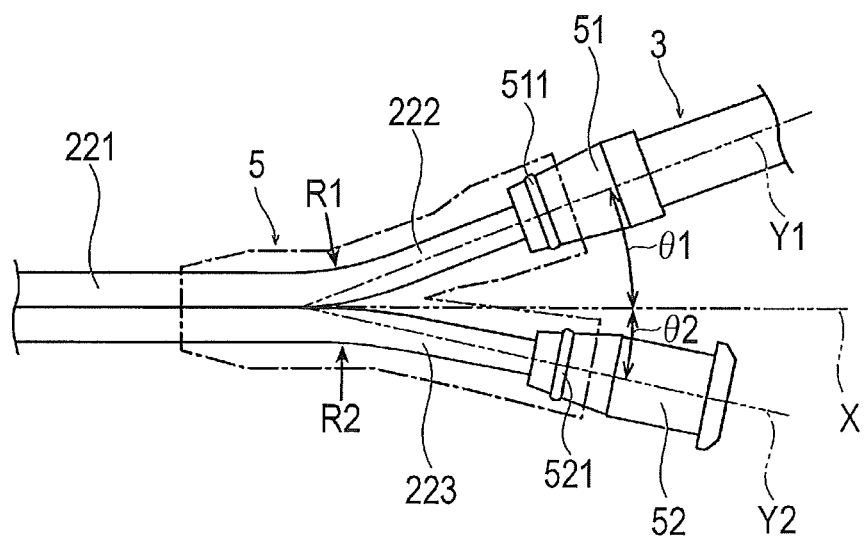
FIG. 7 is a plan view illustrating a hub of a modification example of the medical device according to the embodiment.

In a modification example illustrated in FIG. 7, the medical device is configured to satisfy a relationship of |θ2|>0, while Expression (1) is satisfied. In the example in FIG. 7, a direction of the inclination θ1 of the central axis Y1 of the first hub portion 51 with respect to the reference line X is an opposite direction to a direction of the inclination θ2 of the central axis X of the second hub portion 52 with respect to the reference line X. In other words, in a case where the direction of the inclination of θ1 is defined as a plus, the direction of the inclination of θ2 is defined as a minus. In this configuration, it is possible to increase |θ2−θ1| as much as possible, while |θ1| and |θ2| are as small as possible. In this manner, while the bending of the drive shaft 42 and the guide wire W is reduced as much as possible, the angle between the drive shaft 42 and the guide wire W increases, and it is possible to reduce the interference between motion of the external drive device 7 and an operation of the guide wire W as much as possible.

The inclination |θ1| of the first hub portion 51 is preferably 90° or smaller, more preferably, 70° or smaller, and still more preferably, 55° or smaller. The inclination |θ2| of the second connector is preferably 90° or smaller, more preferably, 40° or smaller, and still more preferably, 10° or smaller.

The angle |θ2−θ1| between the first hub portion 51 and the second hub portion 52 is preferably 10° or larger, more preferably, 55° or larger, and still more preferably, 130° or larger. When the angle |θ2−θ1| is too small, the interference of the motion of the external drive device 7 with an operation of the guide wire W occurs.

It is preferable that the first shaft proximal portion 222 and the second shaft proximal portion 223 which are bent in the hub casing 53 are not bent so as to be locally crooked or kinked, but form a curve having curvature in a certain range such that rotation or movement in the axial direction of the drive shaft 42 and the guide wire W is not inhibited. The minimum curvature radius R1 of the first shaft proximal portion 222 in the hub casing 53 is preferably 5 mm or larger, more preferably, 50 mm or larger, and still more preferably, 100 mm or larger. The minimum curvature radius R2 of the second shaft proximal portion 223 in the hub casing 53 is preferably 5 mm or larger, more preferably, 50 mm or larger, and still more preferably, 100 mm or larger.

As illustrated in FIG. 1, the first anti-kink protector 54 surrounds the distal portion of the hub casing 53 and the shaft main body portion 22 that is guided to exit from the hub casing 53 in the distal direction and reduces an occurrence of kinking of the shaft main body portion 22.

There is no particular limitation on constituent materials of the first hub portion 51, the second hub portion 52, the hub casing 53, the tube 32, the inner tube 34, the unit connector 37, and the operation proximal portion 31, and examples thereof include various types of resins such as polyvinyl chloride, polyethylene, polypropylene, cyclic polyolefin, polystyrene, poly-(4-methylpentene-1), polycarbonate, acrylic resin, acrylonitrile-butadiene-styrene copolymer, polyester such as polyethylene terephthalate or polyethylene naphthalate, butadiene-styrene copolymer, or polyamide (for example, nylon 6, nylon 6·6, nylon 6·10, or nylon 12).

Figure 8:
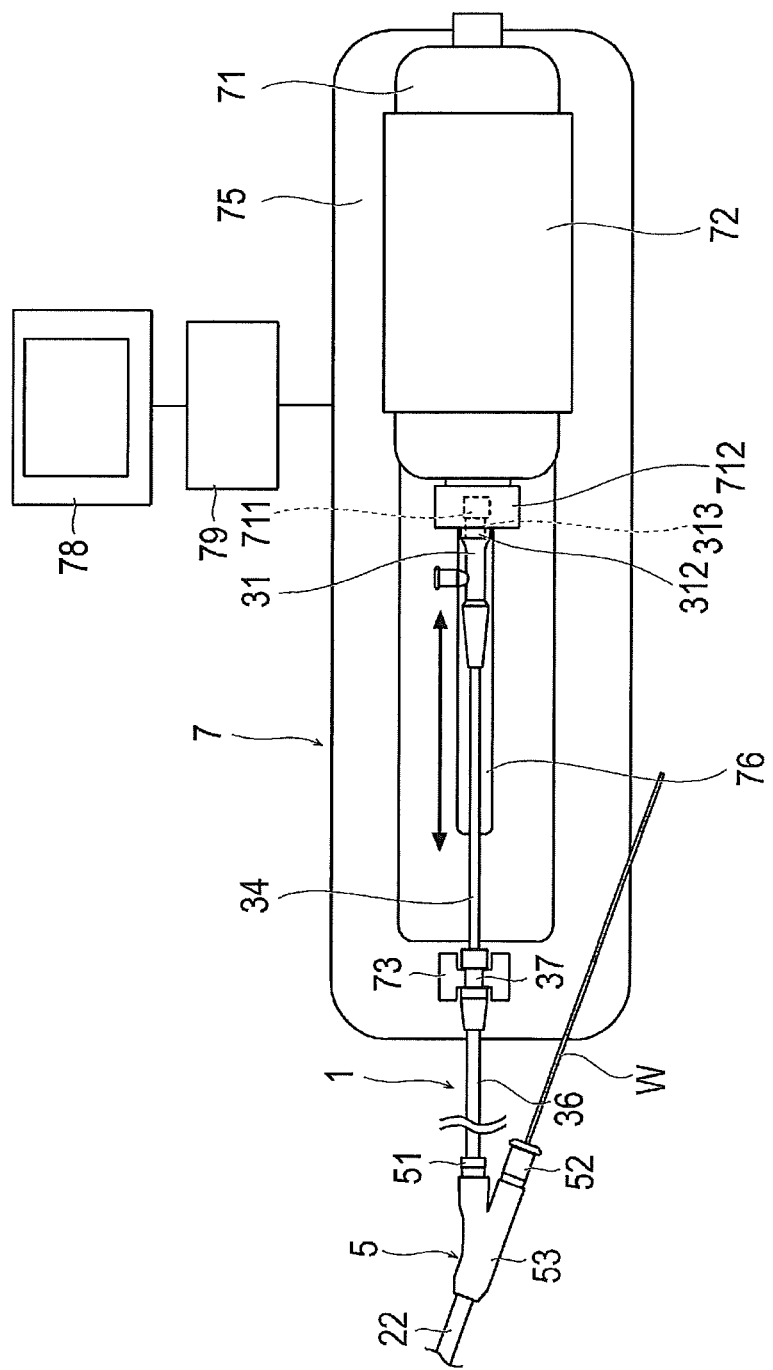
FIG. 8 is a plan view illustrating an external drive device.

As illustrated in FIG. 8, the medical device 1 described above 1 is connected to the external drive device 7 so as to be driven. The external drive device 7 includes, on a base 75, a drive unit 71 in which an external drive source such as a motor is installed and which rotationally drives the drive shaft 42, moving means 72 that grips the drive unit 71 and causes the drive unit to move in the axial direction by a motor or the like (i.e., the moving means 72 can include a motor), and a holding portion 73 that holds a part of the medical device 1 in a position fixing manner. The external drive device 7 is connected to a control unit 79 that controls the drive unit 71 and the moving means 72, and an image obtained by the transducer unit 41 is displayed on a display unit 78 connected to the control unit 79.

The moving means 72 is a transfer mechanism that is configured to grip and fix the drive unit 71 and causes the gripped drive unit 71 to move forward and backward along a groove rail 76 on the base 75.

The drive unit 71 includes a driving female connector 711 to which the hub-side connector 313 of the medical device 1 is connectable, and a joint connection section 712 that is connectable to a joint 312 of the medical device 1, and it is possible to transmit and receive a signal to and from the transducer unit 41 through the connection, and it is possible to rotate the drive shaft 42.

As illustrated in FIGS. 8 and 9, ultrasonic scanning in the medical device 1 is performed when the moving means 72 is caused to move in the axial direction such that rotary motion of the motor in the drive unit 71 is transmitted to the drive shaft 42, and the housing 412 fixed at the distal end of the drive shaft 42 rotates. In this manner, the ultrasound transducer 411 provided in the housing 412 moves and rotates in a longitudinal direction thereof, and it is possible to perform scanning in a substantially radial direction with ultrasound waves that are transmitted and received by the ultrasound transducer 411. In this manner, it is possible to acquire a 360°-cross-sectional image of surrounding tissue to any position in the axial direction in the blood vessel in a scanning manner.

Figure 10:
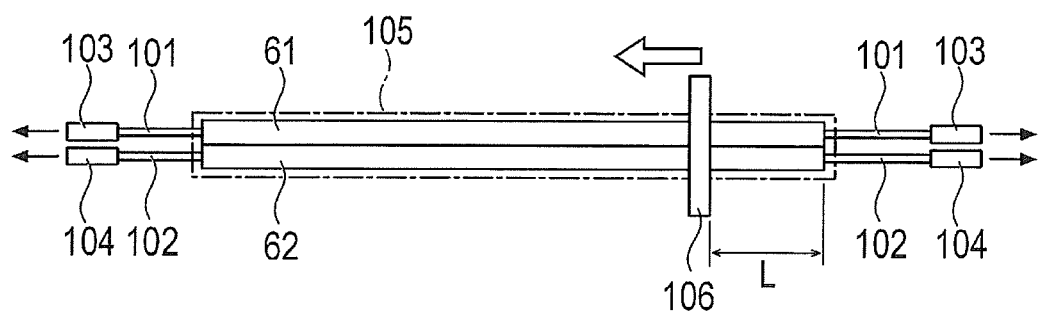
FIG. 10 is a schematic plan view for illustrating a method for manufacturing the medical device.

Next, referring to FIG. 10, a method for manufacturing the medical device 1 according to a disclosed embodiment representing an example of the inventive manufacturing method, will be described.

First, through a known extrusion molding method, a first pipe body (tube) 61 is molded on the outer periphery of a first core bar 101, and a second pipe body (tube) 62 is molded on the outer periphery of a second core bar 102. Next, as illustrated in FIG. 10, both ends of the first core bar 101 are fixed to a first stretching chuck 103, and both ends of the second core bar 102 are fixed to a second stretching chuck 104. Then, the first stretching chuck 103 and the second stretching chuck 104 are pulled such that a tensile force of a load which is heavier to some extent than that of a yield point of the first pipe body 61 and the second pipe body 62 is applied to the first pipe body 61 and the second pipe body 62. In this manner, the first pipe body 61 and the second pipe body 62 are linearly stretched to some extent and have a stable shape (linear process).

Next, the first pipe body 61 and the second pipe body 62 are covered with a heat shrinkable tube 105 having a diameter that decreases when heat is applied. Next, a heating unit 106 such as a heater is caused to approach the outer periphery of the first pipe body 61 and the second pipe body 62 and is disposed at a position that is away from (spaced from) one end side by a predetermined length L (for example, 30 mm). Then, while the heating unit 106 performs heating, the heating unit is caused to move to the other end as shown by the outline arrow next to the heating unit 106 in FIG. 10. In this manner, the heat shrinkable tube 105 shrinks such that the first pipe body 61 and the second pipe body 62 are pressed against each other and heat-welded so as to have an integral, one-piece, unitary structure (heat-welding process). The larger the stretching amount of the first stretching chuck 103 and the second stretching chuck 104, the smaller the outer diameters and the inner diameters of regions of the first pipe body 61 and the second pipe body 62 which are heated. Therefore, control of the stretching amount and a moving speed of the heating unit 106 enables the pipe bodies to have the outer diameters and the inner diameters which are different depending on a position in the axial direction.

As an example, while the first core bar 101 and the second core bar 102 are stretched by the first stretching chuck 103 and the second stretching chuck 104, the heating unit 106 is caused to move along the first pipe body 61 and the second pipe body 62 such that the first pipe body 61 and the second pipe body 62 are heat-welded together. In this manner, it is possible to form the shaft main body portion 22 having an outer diameter and an inner diameter that decrease such that the main body portion has a tapered shape in the distal direction.

In addition, as another example, while the second core bar 102 is stretched by the second stretching chuck 104 without stretching the first core bar 101, the heating unit 106 is caused to move such that the first pipe body 61 and the second pipe body 62 are heat-welded. In this manner, it is possible to form the shaft main body portion 22 having an outer diameter and an inner diameter on the second pipe body 62 side that decrease such that the main body portion has a tapered shape in the distal direction, and it is possible to form the shaft main body portion 22 having an outer diameter and an inner diameter on the first pipe body 61 side that is constant in the axial direction.

As described above, while the stretching amounts of the first core bar 101 and the second core bar 102 are adjusted, the heating unit 106 is caused to move such that the heat-welding is performed. In this manner, without using a metal wire having a certain rigidity, or joining or combining different materials, it is possible to relatively easily impart desired physical properties to the shaft main body portion 22. In other words, the first pipe body 61 and the second pipe body 62 are heat-welded so as to form the shaft main body portion 22 having a double-lumen structure, and thereby it is difficult to impart desired physical properties without adding another member and changing the outer diameter. However, since it is possible to rather easily change the outer diameter and the inner diameter, it is less necessary to add the other member and it is possible to impart the desired physical properties without any problems.

Next, when the heating by the heating unit 106 is stopped and the first stretching chuck 103 and the second stretching chuck 104 are further pulled, the first core bar 101 and the second core bar 102 are further stretched and the diameter decreases, and the first core bar 101 and the second core bar 102 are separated from inner peripheral surfaces of the first pipe body 61 and the second pipe body 62 and are broken. Then, the first core bar 101 and the second core bar 102 are detached from the first stretching chuck 103 and the second stretching chuck 104, and the first core bar 101 and the second core bar 102 are pulled out from the first pipe body 61 and the second pipe body 62 (stretching/removing process). Then, the heat shrinkable tube 105 is removed, and the shaft main body portion 22 is formed in a region having a length L that is not heated, while the remaining region of the first pipe body 61 and the second pipe body 62 is heat-welded or partially heat-welded in the axial direction. The region of the first pipe body 61 that is not heated is the first shaft proximal portion 222, the region of the second pipe body 62 that is not heated is the second shaft proximal portion 223, and the region of the first pipe body 61 and the second pipe body 62 that is heated and heat-welded is the intermediate shaft portion 221. As shown in FIG. 4, the regions of the first and second pipe bodies 61, 62 that are not heated represent the bifurcated first and second shaft proximal portions 222, 223, while the regions of the first and second pipe bodies 61, 62 that are heated are not bifurcated and are connected or heat-welded (integrated) together. The non-bifurcated part is immediately adjacent the bifurcated first and second shaft proximal portions 222, 223.

It is possible to perform, in a series of operations, the linear process of temporary stretching by the first core bar 101 and the second core bar 102, the heat-welding process by the heating unit 106, and the stretching/removing process of stretching the first core bar 101 and the second core bar 102 until the core bars are broken and removing the core bars from the first pipe body 61 and the second pipe body 62, and thus it is possible to efficiently manufacture the intermediate shaft portion 221 having a desired outer diameter and inner diameter.

Then, the first hub portion 51 is interlocked with the first shaft proximal portion 222 in an airtight manner and the second hub portion 52 is interlocked with the second shaft proximal portion 223 in an airtight manner.

Figure 11:
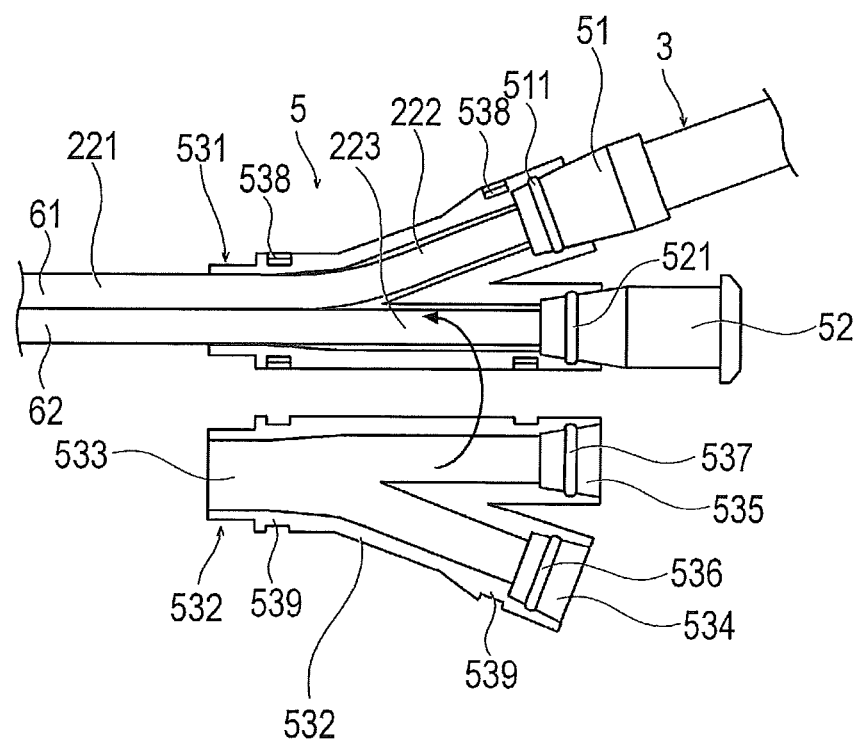
FIG. 11 is a plan view illustrating a state before the hub casing is attached to a first hub portion, a second hub portion, and a shaft main body portion.
Figure 12:
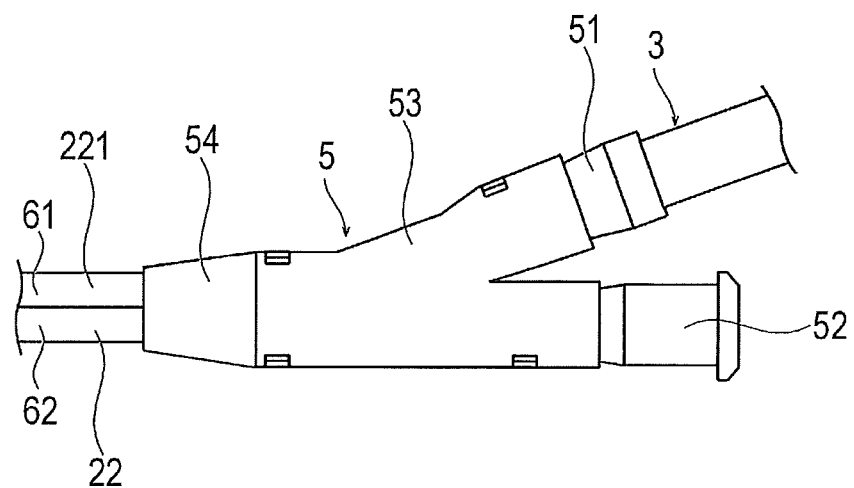
FIG. 12 is a plan view illustrating a state in which the hub casing is attached to the first hub portion, the second hub portion, and the shaft main body portion.

Next, as illustrated in FIG. 11, in a state in which the first interlocking convex portion 511 of the first hub portion 51 is fitted in the first interlocking concave portion 536 of the first casing 531, and the second interlocking convex portion 521 of the second hub portion 52 is fitted in the second interlocking concave portion 537 of the first casing 531, the interlocking hook 538 is interlocked with the interlocking stepped portion 539 such that the first casing 531 and the second casing 532 are interlocked with each other. Then, as illustrated in FIG. 12, the first anti-kink protector 54 is attached to surround the distal portion of the hub casing 53 and the shaft main body portion 22 that is guided to exit from the hub casing 53 in the distal direction.

When the hub casing 53 is attached to the first hub portion 51 and the second hub portion 52, the first hub portion 51 and the second hub portion 52 are fixed to the hub casing 53 so as not to be dropped off or separated from the hub casing 53. In addition, since the first shaft proximal portion 222 is interlocked with the first hub portion 51 in an airtight manner, and the second shaft proximal portion 223 is interlocked with the second hub portion 52 in an airtight manner, it is unnecessary to use the airtight structure in the hub casing 53, and thus it is possible to simplify a configuration of the hub casing 53. Further, since the first casing 531 and the second casing 532 are configured to have the split type structure so as to interpose the outer peripheral surfaces of the shaft main body portion 22, the first hub portion 51, and the second hub portion 52 from both sides, it is possible to easily cover the hub casing 53 in a state in which the first hub portion 51 and the second hub portion 52 are interlocked with the shaft main body portion 22. At this time, the hub casing 53 has the split type structure, and thereby it is rather easy to position the bifurcated portion of the shaft main body portion 22 inside the hub casing 53, and it is fairly easy to dispose the first hub portion 51 and the second hub portion 52 at a predetermined angle and to fix the hub portions to the hub casing 53. In other words, in a case where the hub casing is not split, the first shaft proximal portion 222 and the second shaft proximal portion 223 need to be inserted into an opening portion of the hub casing on the distal side, to move in two different bifurcating directions in the hub casing 53, and to be guided to exit to another opening portion on the proximal side in a state in which the first hub portion 51 and the second hub portion 52 are not interlocked with each other. In this manner, it is difficult to perform work. In order to perform work of interlocking the first hub portion 51 and the second hub portion 52 with the first shaft proximal portion 222 and the second shaft proximal portion 223 which are guided to exit from the opening portion on the proximal side, the first shaft proximal portion 222 and the second shaft proximal portion 223 temporarily need to be guided to exit from the hub casing in the proximal direction by a length longer than necessary. Therefore, when a region (the first shaft proximal portion 222 and the second shaft proximal portion 223), in which the shaft main body portion 22 is to be bifurcated, needs to be longer than necessary, the hub casing is pushed such that the shaft main body portion 22 moves to an appropriate position after the first hub portion 51 and the second hub portion 52 are interlocked with each other, there is a high possibility that the bifurcated portion of the shaft main body portion 22 reaches a position on the distal side from the hub casing 53. By comparison, in the embodiment, the hub casing 53 has the split type structure, and thereby it is easy to position the bifurcated portion of the shaft main body portion 22, which has rigidity that locally changes, inside the hub casing 53. In this manner, the shaft main body portion 22 can exhibit high pushing performance, thus, it is possible to reduce an occurrence of a kink, and it is possible to reduce an occurrence of attachment or the like of thrombus in a recessed portion of the bifurcated portion.

Then, while the shaft distal portion 21 and the distal tip 23 are heat-welded to the shaft main body portion 22 on the distal side, and the imaging core 4 is inserted into the image acquiring lumen 25 from the first hub portion 51, the operation unit 3 is interlocked with the first hub portion 51 and the manufacturing of the medical device 1 is completed.

Next, an operation performed when biological tissue from a body lumen of the blood vessel or the like is observed by using the medical device 1 according to the embodiment will be described.

First, before the shaft portion 2 of the medical device 1 is inserted into the lumen, a priming operation of filling the medical device 1 with saline is performed. The priming operation enables the ultrasound waves to be transmitted from the ultrasound transducer 411, and air in the medical device 1 is removed such that air is prevented from entering the lumen of the blood vessel or the like.

Figure 13:
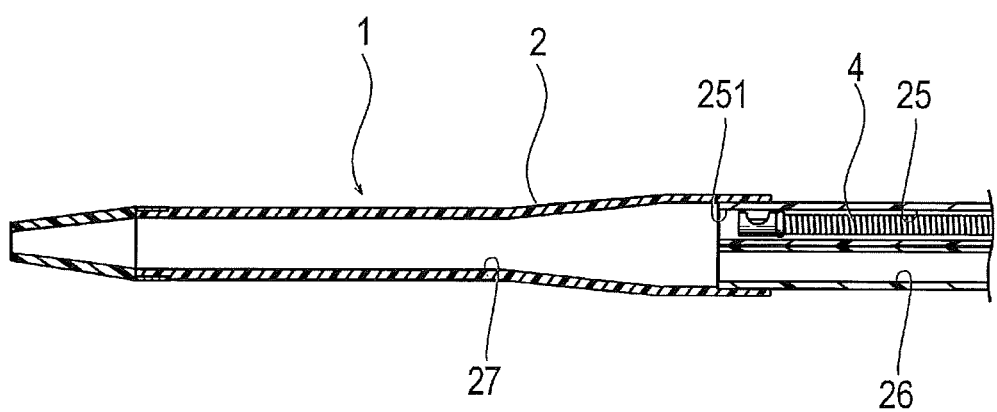
FIG. 13 is a longitudinal-sectional view illustrating a state in which priming is performed on the medical device according to the embodiment.

As illustrated in FIGS. 9 and 13, in order to perform the priming, in a state in which the operation proximal portion 31 is most tensioned to the proximal side from the unit connector 37, that is, in a state in which the inner tube 34 is tensioned from the outer tube 32 to the greatest extent, the saline is injected, by using a syringe or the like, via an instrument that includes a tube (not illustrated) and a three-way stopcock (not illustrated) which are connected to the port 311 of the operation proximal portion 31. The injected saline fills the image acquiring lumen 25 through the first hub portion 51 from the operation proximal portion 31. The saline in the image acquiring lumen 25 flows into the common lumen 27, and further flows into the guide wire lumen 26 from the common lumen 27. When the guide wire lumen 26 is filled with the saline, the saline flows out from the opening portion of the second hub portion 52. When the saline is further injected after checking of the flowing-out of the saline from the opening portion of the second hub portion 52, the common lumen 27 is filled with the saline and the saline flows out from the distal opening portion 28. In this manner, the filling of the saline is checked, and the priming is completed. The saline flows out from the distal opening portion 28 before the saline flows out from the second hub portion 52 in some cases. As described above, since the image acquiring lumen 25 and the guide wire lumen 26 converge in the common lumen 27, it is possible to perform priming of both of the image acquiring lumen 25 and the guide wire lumen 26 by the injection at once from one side and high operability is achieved. That is, priming of both the image acquiring lumen 25 and the guide wire lumen 26 can be accomplished by injecting saline at a single location (e.g., a location in communication with the image acquiring lumen 25). In addition, the flowing-out of the saline from the second hub portion 52 and the distal opening portion 28 is checked, and thereby it is possible to reliably perform the priming. The priming operation enables the air in the medical device 1 to be removed, and it is possible to prevent air from entering the lumen. Note that it is possible to perform the priming in a state in which the transducer unit 41 is caused to move in the common lumen 27.

In addition, the priming may be performed from the second hub portion 52 of the proximal portion of the guide wire lumen 26. In this case, the saline is injected by using a syringe or the like via an instrument that includes a tube and a three-way stopcock (not illustrated) which are connected to the second hub portion 52. The injected saline fills the guide wire lumen 26 through the second hub portion 52. The saline flowing in the guide wire lumen 26 flows into the common lumen 27, the common lumen 27 is filled with the saline, and then the saline flows out from the distal opening portion 28. In this manner, the filling of the saline is checked, and the priming is completed. As described above, the priming is not only performed in the image acquiring lumen 25, but also can be performed in the common lumen 27 by using the guide wire lumen 26. In a case where the priming is performed from the guide wire lumen 26, a pressure loss is less than that in a case where the priming is performed from the image acquiring lumen 25 in which the drive shaft 42 is present, thus it is possible to easily perform the priming with little force, and the high operability is achieved.

Because the image acquiring lumen 25 has high pressure loss with the presence of the drive shaft 42, the priming is not necessarily limited to complete priming from the guide wire lumen 26 side; however, when the medical device 1 is used, pressure is applied from the distal opening portion 28 side of the common lumen 27, the air in the image acquiring lumen 25 moves to the proximal side, and thus the state is considered that no problem arises. When the priming is performed from the second hub portion 52 in a state in which the distal opening portion 28 is closed, the saline flowing in the common lumen 27 flows into the image acquiring lumen 25, and thus it is possible to perform the priming of the guide wire lumen 26 and the image acquiring lumen 25 at once from the guide wire lumen 26 side.

Next, as illustrated in FIG. 8, the medical device 1 is interlocked with the external drive device 7 that is covered with a sterilized bag (not illustrated) made of polyethylene. In other words, the joint 312 of the operation proximal portion 31 of the medical device 1 is connected to the joint connection section 712 of the drive unit 71. In this manner, it is possible to transmit and receive a signal between the transducer unit 41 and the external drive device 7, and it is possible to rotate the drive shaft 42. When the unit connector 37 is fitted into the holding portion 73, the connection is completed.

Figure 14:
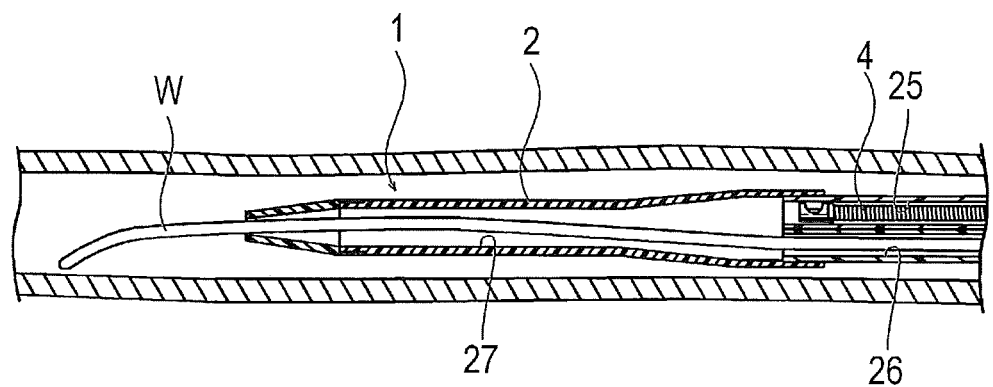
FIG. 14 is a longitudinal-sectional view illustrating a state in which the medical device according to the embodiment is inserted into a blood vessel.

Next, the guide wire W is inserted into the blood vessel via a sheath that is percutaneously inserted into the blood vessel through Seldinger method. Then, the proximal portion of the guide wire W is inserted from the distal opening portion 28 of the medical device 1, and is inserted into the guide wire lumen 26 via the common lumen 27. As illustrated in FIG. 14, since the imaging core 4 is not positioned in the common lumen 27, it is possible to reduce damage to the imaging core 4, and the movement of the guide wire W is not inhibited. In addition, since the first pipe body 61 and the second pipe body 62 have different colors and have transparency to the extent that the inside can be observed, it is possible to insert the guide wire W into the guide wire lumen 26 without inserting into the image acquiring lumen 25 from the common lumen 27 while the inside of the shaft portion 2 is observed after the guide wire is inserted from the distal opening portion 28 formed in the distal tip 23. When the guide wire W inserted from the distal opening portion 28 is inserted into the guide wire lumen 26 from the common lumen 27, the shaft portion is distorted, and thereby it is possible for the guide wire W not to move into the image acquiring lumen 25 but to move toward the guide wire W. That is, by virtue of the configuration of the guide wire lumen 26 and the image acquiring lumen 25, it is easier for the guide wire W inserted through the distal opening portion 28 to enter the guide wire lumen 26 than it is to enter the image acquiring lumen 25.

After the guide wire W is guided to exit from the first hub portion 51 on the proximal side, the medical device 1 is pushed forward along the guide wire W, and the distal portion of the medical device 1 is disposed on a rear side (distal side) from the target lesion to be observed. At this time, since the first hub portion 51 and the second hub portion 52 extend in different directions, it is possible for the operator to operate the guide wire W without interfering with the operation unit 3 or the external drive device 7. In addition, since the guide wire lumen 26 is opened in the second hub portion 52 on the hand side, it is possible to rather easily interchange the guide wire W without wetting the wire with the blood leaking from the sheath. Therefore, the guide wire W having a desired load-shape is used (e.g., a guide wire having a thickness that provides the desired pushing force and having a desired tip angle shape), and thereby it is possible to cause the medical device 1 to efficiently reach a deep portion of a complex region. In addition, since the guide wire lumen 26 is opened in the second hub portion 52 on the hand side, it is possible to supply a contrast agent or medicine via the guide wire lumen 26 and to release the contrast agent or medicine to a living body from the distal opening portion 28.

Figure 15:
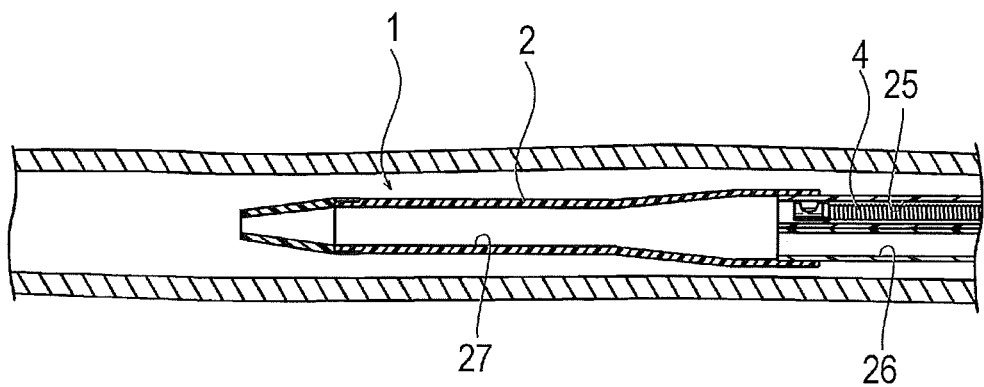
FIG. 15 is a longitudinal-sectional view illustrating the medical device which is in a state in which a guide wire moves to the proximal side from a common lumen.

Next, as illustrated in FIG. 15, while the shaft portion 2 is held not to be moved in the blood vessel, the guide wire W is caused to move in the proximal direction until the distal end of the guide wire W is accommodated in the guide wire lumen 26. At this time, the guide wire W may be completely pulled out from the guide wire lumen 26. Even when the guide wire W is completely pulled out from the guide wire lumen 26, the guide wire lumen 26 is opened in the second hub portion 52 in the hand side, and thus it is possible to insert the guide wire W again.

Figure 16:
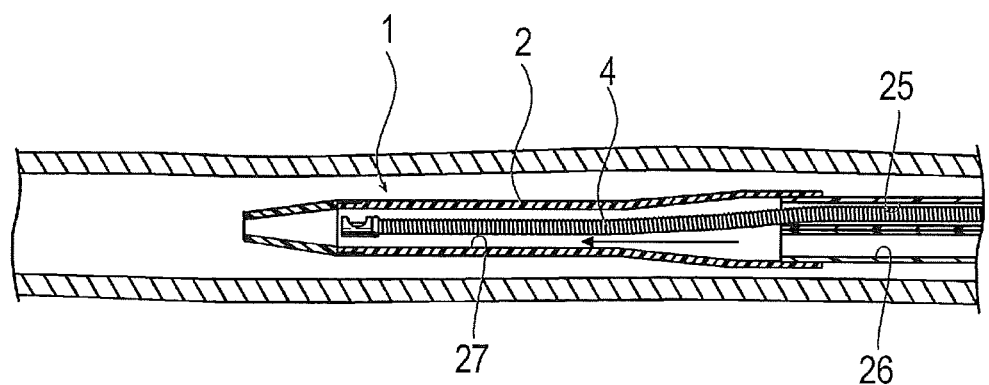
FIG. 16 is a longitudinal-sectional view illustrating a state in which an imaging core moves forward in the medical device according to the embodiment.

In this state, the drive unit 71 moves to the distal side along the groove rail 76 on the base 75 (refer to FIG. 8) while the shaft portion 2 is held (i.e., noted moved). In this manner, the operation proximal portion 31 is caused to move to the distal side and enters a state in which the inner tube 34 is pushed into the outer tube 32 to the greatest extent. In this manner, as illustrated in FIG. 16, the imaging core 4 moves to the distal side of the common lumen 27. That is, the imaging core 4 moves to a position distal of the distal-most end of the image acquiring lumen 25 as shown in FIG. 14. At this time, since the guide wire W is not positioned in the common lumen 27, it is possible to reduce damage to the imaging core 4, and the motion of the imaging core 4 is not inhibited by the guide wire W.

Figure 17:
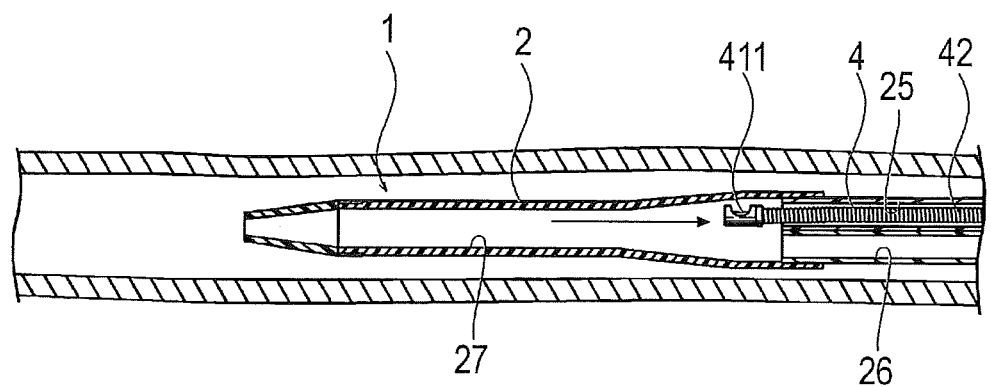
FIG. 17 is a longitudinal-sectional view illustrating a state in which an image is acquired by an imaging core of the medical device according to the embodiment.

Next, as illustrated in FIGS. 9 and 17, the drive shaft 42 is pulled back while the drive shaft 42 is rotated by the drive unit 71. In this manner, the ultrasound transducer 411 is caused to move toward the proximal side from the target lesion in the axial direction while the radial scanning is performed by the ultrasound transducer 411, and thus images of biological tissue including the target lesion are acquired in the axial direction of the lumen. At this time, since the drive shaft 42 is curved in the hub 5, but is curved in a certain extent or controlled manner without an influence on the rotation, it is possible to acquire stable image without having the rotation unevenness or the jumping.

Then, the medical device 1 is pulled out from the blood vessel, and then the operation of the medical device 1 is completed.

As described above, in the medical device 1 according to the embodiment, the first hub portion 51 is interlocked, in the airtight manner, with the first shaft proximal portion 222 in which the drive shaft 42 is accommodated and the second hub portion 52 is interlocked, in the airtight manner, with the second shaft proximal portion 223 into which the guide wire W is inserted, and the first hub portion 51 and the second hub portion 52 are collectively covered with the hub casing 53. Therefore, it is fairly easy to interchange the guide wire W on the front side of the operator, in a state in which the medical device 1 is inserted into the living body, and thus it is possible to release the contrast agent, medicine, or the like to a living body from the distal opening portion 28 via the guide wire lumen 26. When it is possible to interchange the guide wire W, it is possible to use a guide wire W having a desired load-shape, and thereby it is possible to cause the medical device 1 to efficiently reach the deep portion of the complex region. In addition, since the first shaft proximal portion 222 of the shaft main body portion 22 is directly interlocked with the first hub portion 51, the distortion or sliding failure of the drive shaft 42 in the hub casing 53 is unlikely to occur, and thus it is possible to acquire a good-quality image. In addition, since the second shaft proximal portion 223 of the shaft main body portion 22 is directly interlocked with the second hub portion 52, the distortion or the sliding failure of the guide wire W is unlikely to occur in the hub casing 53, and thus it is possible to achieve a high-quality operation of the guide wire W. In addition, since the first hub portion 51 is interlocked with the first shaft proximal portion 222 in the airtight manner, and the second hub portion 52 is interlocked with the second shaft proximal portion 223 in the airtight manner, the hub casing 53 that collectively covers the first shaft proximal portion 222, the second shaft proximal portion 223, the first hub portion 51, and the second hub portion 52 does not need to have the sealing performance, but can have a simplified configuration, and can realize simplification in the manufacturing process or reduction in costs.

In addition, since the shaft main body portion 22 is provided with two longitudinally extending and side-by-side regions having different colors, one region of one color in which the image acquiring lumen 25 is provided and the other region of a different color in which the guide wire lumen 26 is provided, it is possible to rather easily visually discriminate between the image acquiring lumen 25 and the guide wire lumen 26, and it is easy to insert the guide wire W into the guide wire lumen 26 when the guide wire W is inserted into the guide wire lumen 26 from the distal opening portion 28 of the shaft distal portion 21 on the distal side.

In addition, in a case where the axis line (central axis) of the shaft main body portion 22 in the distal portion of the hub casing 53 is set to the reference line X, θ1 represents the inclination of the central axis Y1 of the first hub portion 51 with respect to the reference line X, and θ2 represents the inclination of the central axis Y2 of the second hub portion 52 with respect to the reference line X, the relationship of |θ1|>|θ2| is satisfied. Therefore, even in the over-the-wire structure in which the opening portions of the guide wire lumen 26 and the image acquiring lumen 25 on the proximal side are provided in the same hub 5, the first hub portion 51 and the second hub portion 52 are formed in the different directions. Therefore, it is possible to maintain the high operability without the interference of the motion of the drive shaft 42 and the transducer unit 41 (imaging unit) via the image acquiring lumen 25 with the operation of the guide wire W via the guide wire lumen 26. In addition, the relationship of |θ1|>|θ2| is satisfied, and thereby it is possible to maintain the operability of the guide wire W normally having rigidity higher than that of the drive shaft 42, to the highest extent.

In addition, the hub casing 53 is configured to have the split type structure so as to interpose the outer peripheral surfaces of the first hub portion 51 and the second hub portion 52 from both sides, and thus it is possible to relatively easily dispose, inside the hub casing 53, the first hub portion 51 and the second hub portion 52 which are inclined in different directions, with the shaft main body portion 22. Since it is possible to fairly easily dispose the first hub portion 51, the second hub portion 52, and the shaft main body portion 22 inside the hub casing 53, it is possible to reliably hold the bifurcated region of the proximal portion of the shaft main body portion 22 inside the hub casing 53. Therefore, a bifurcated portion of the shaft main body portion 22, which has relatively low rigidity, is not positioned on the distal side from the hub casing 53. In this manner, it is possible to exhibit high pushing performance, it is possible to reduce an occurrence of a kink, and it is possible to reduce an occurrence of attachment or the like of thrombus in a recessed portion of the bifurcated portion.

In addition, When the direction of the inclination of the central axis Y1 of the first hub portion 51 with respect to the reference line X is the opposite direction to the direction of the inclination of the central axis Y2 of the second hub portion 52 with respect to the reference line X, the angle between the drive shaft 42 and the guide wire W increases while the bending of the drive shaft 42 and the guide wire W is reduced as much as possible, and thus it is possible to reduce an occurrence of interference of motion of the transducer unit 41 (imaging unit) via the image acquiring lumen 25 with the operation of the guide wire W via the guide wire lumen 26, as much as possible.

The present invention is not limited to the embodiment described above, and it is possible for those skilled in the art to perform various modifications within the technical ideas of the present invention. For example, in the embodiment described above, a case in which the present invention is applied to the ultrasound catheter is described, but it is also possible to apply the invention to a device that acquires images by using beams, such as an optical coherence tomography (OCT) diagnostic apparatus or an optical frequency domain imaging (OFDI) diagnostic apparatus.

What is claimed is:

1. An image-acquiring medical device insertable into a body lumen to acquire images inside the body lumen, the image-acquiring medical device comprising:

a shaft main body portion possessing a distal end at one end of the shaft main body portion and a proximal end at an opposite end of the shaft main body portion, the shaft main body portion including two lumens extending throughout a length of the shaft main body portion from the distal end of the shaft main body portion to the proximal end of the shaft main body portion, the two lumens of the shaft main body portion being separated from one another along the length of the shaft main body portion by a wall, the two lumens in the shaft main body portion comprising an image acquiring lumen and a guide wire lumen for receiving a guide wire;

a proximal portion of the shaft main body portion including a first shaft proximal portion, in which a portion of the image acquiring lumen is disposed, and a second shaft proximal portion, in which a portion of the guide wire lumen is disposed, the first shaft proximal portion and the second shaft proximal portion being bifurcated;

a drive shaft rotatably positioned in the image acquiring lumen and axially movable in the image acquiring lumen, the drive shaft possessing a distal end;

a transducer unit configured to acquire images, the transducer unit being fixed to the distal end of the drive shaft so that axial and rotational movement of the drive shaft results in axial and rotational movement respectively of the transducer unit;

a shaft distal portion connected to the distal end of the shaft main body portion, the shaft distal portion possessing a distal end and a proximal end, the shaft distal portion including only a single lumen, the single lumen in the shaft distal portion extending from the proximal end of the shaft distal portion to the distal end of the shaft distal portion, the single lumen in the shaft distal portion having an open distal end at the distal end of the shaft distal portion and having an open proximal end at the proximal end of the shaft distal portion, the single lumen in the shaft distal portion being open to outside the shaft distal portion only by way of the open distal end of the lumen at the distal end of the shaft distal portion, the single lumen in the shaft distal portion communicating with both the guide wire lumen and the image acquiring lumen so that: i) the guide wire is guidable along the guide wire lumen in the shaft main body portion and along the single lumen in the shaft distal portion while extending distally beyond the open distal end of the shaft distal portion and proximally beyond a proximal end of the second shaft proximal portion; and ii) the drive shaft is positionable in the image acquiring lumen in the shaft main body portion and in the single lumen in the shaft distal portion so that the transducer unit is positioned in the single lumen in the shaft distal portion;

a hub that includes a first hub portion interlocked with the first shaft proximal portion and a second hub portion interlocked with the second shaft proximal portion, the first hub portion possessing a central axis and the second hub portion possessing a central axis;

wherein the shaft main body portion possesses an axis line constituting a reference line;

wherein an inclination of the central axis of the first hub portion with respect to the reference line is represented by an angle $\theta 1$;

wherein an inclination of the central axis of the second hub portion with respect to the reference line is represented by $\theta 2$; and wherein a relationship of $|\theta 1| > |\theta 2|$ is satisfied.

2. The medical device according to claim 1, wherein the hub further comprises a hub casing that collectively covers the first shaft proximal portion, the second shaft proximal portion, the first hub portion, and the second hub portion.

3. The medical device according to claim 1, wherein the hub further comprises a hub casing that collectively covers the bifurcated first and second shaft proximal portions, the first hub portion, the second hub portion and a non-bifurcated part of the shaft distal portion positioned distal of the bifurcated first and second shaft proximal portions.

4. The medical device according to claim 3, wherein the hub casing comprises first and second casings that are connected to one another, wherein the first and second casings each surround at least a part of the bifurcated first and second shaft proximal portions, at least a part of the first hub portion, at least a part of the second hub portion and a non-bifurcated part of the shaft distal portion positioned distal of the bifurcated first and second shaft proximal portions.

5. The medical device according to claim 3, wherein the hub casing comprises first and second casings that are connected to one another, wherein one end portion of the hub casing covers an outer periphery of the first hub portion and an outer periphery of the second hub portion, the hub casing possessing an outer dimension that increases towards the one end portion.

6. The medical device according to claim 1, wherein a direction of the inclination of the central axis of the first hub portion with respect to the reference line is an opposite direction to a direction of the inclination of the central axis of the second hub portion with respect to the reference line.

7. The medical device according to claim 1, the hub also comprising a hub casing surrounding a distal portion of the first hub portion and surrounding a distal portion of the second hub portion;

the hub casing being fixed to the distal portion of the first hub portion by a convex portion on one of an exterior of the first hub portion and an interior of the hub casing being fitted into a concave portion on the other of the exterior of the first hub portion and the interior of the hub casing; and the hub casing being fixed to the distal portion of the second hub portion by a convex portion on one of an exterior of the second hub portion and the interior of the hub casing being fitted into a concave portion on the other of the exterior of the second hub portion and the interior of the hub casing.

8. The medical device according to claim 7, wherein a proximal portion of both the first hub portion and second hub portion is exposed outside the hub casing.

9. The medical device according to claim 1, wherein the proximal portion of the shaft main body portion includes a non-bifurcated part immediately adjacent the bifurcated first and second shaft proximal portions, the bifurcated first and second shaft proximal portions possessing respective outer surfaces that are spaced apart from one another, and that are covered by the hub casing, the hub casing also covering the non-bifurcated part of the shaft main body portion.

10. The medical device according to claim 1, wherein the hub also includes a hub casing comprised of a distal side fitting portion, a first hub fitting portion and a second hub fitting portion, the distal side fitting portion surrounding an outer peripheral surface of a proximal portion of the shaft main body portion, the first hub fitting portion surrounding an outer peripheral surface of a distal portion of the first hub portion, the second hub fitting portion surrounding an outer peripheral surface of a distal portion of the second hub portion, the distal portion of the first hub portion including a circumferentially extending and outwardly projecting projection positioned in a circumferentially extending recess in an inner peripheral surface of the first hub fitting portion, the distal portion of the second hub portion including a circumferentially extending and outwardly projecting projection positioned in a circumferentially extending recess in an inner peripheral surface of the second hub fitting portion.

11. The medical device according to claim 1, wherein the hub also includes a hub casing comprised of a distal side fitting portion, a first hub fitting portion and a second hub fitting portion, the distal side fitting portion surrounding an outer peripheral surface of a proximal portion of the shaft main body portion, the first hub fitting portion surrounding an outer peripheral surface of a distal portion of the first hub portion, the second hub fitting portion surrounding an outer peripheral surface of a distal portion of the second hub portion, the first and second hub portions each possessing an outer peripheral surface, the first and second hub fitting portions each possessing an inner peripheral surface, further comprising:

a first interlock structure between the outer peripheral surface of the first hub portion and the inner peripheral surface of the first hub fitting portion to interlock the first hub portion and the first hub fitting portion to one another, the first interlock structure including a circumferentially extending first projection that is positioned in a circumferentially extending first recess, the first projection being provided on one of the inner peripheral surface of the first hub fitting portion and the outer peripheral surface of first hub portion while the first recess is provided on the other of the inner peripheral surface of the first hub fitting portion and the outer peripheral surface of first hub portion; and a second interlock structure between the outer peripheral surface of the second hub portion and the inner peripheral surface of the second hub fitting portion to interlock the second hub portion and the second hub fitting portion to one another, the second interlock structure including a circumferentially extending second projection that is positioned in a circumferentially extending second recess, the second projection being provided on one of the inner peripheral surface of the second hub fitting portion and the outer peripheral surface of second hub portion while the second recess is provided on the other of the inner peripheral surface of the second hub fitting portion and the outer peripheral surface of second hub portion.

12. The medical device according to claim 1, wherein the hub also includes a hub casing comprised of a distal side fitting portion, a first hub fitting portion and a second hub fitting portion, the distal side fitting portion surrounding an outer peripheral surface of a proximal portion of the shaft main body portion, the first hub fitting portion surrounding an outer peripheral surface of a distal portion of the first hub portion, the second hub fitting portion surrounding an outer peripheral surface of a distal portion of the second hub portion, the first hub fitting portion possessing an outer peripheral surface and the second hub fitting portion possessing an outer peripheral surface, the hub casing being configured so that the outer peripheral surface of a proximal-most portion of the first hub fitting portion is spaced from the outer peripheral surface of a proximal-most portion of the second hub fitting portion such that a space exists between the outer peripheral surface of the proximal-most portion of the first hub fitting portion and the outer peripheral surface of the proximal-most portion of the second hub fitting portion.

13. An image-acquiring medical device insertable into a body lumen to acquire images inside the body lumen, the image-acquiring medical device comprising:
a shaft main body portion possessing a distal end at one end of the shaft main body portion and a proximal end at an opposite end of the shaft main body portion, the shaft main body portion including two lumens extending throughout a length of the shaft main body portion from the distal end of the shaft main body portion to the proximal end of the shaft main body portion, the two lumens of the shaft main body portion being separated from one another along the length of the shaft main body portion by a wall, the two lumens in the shaft main body portion comprising an image acquiring lumen and a guide wire lumen for receiving a guide wire, the image acquiring lumen having an open distal end, the guide wire lumen having an open distal end;
a proximal portion of the shaft main body portion including a first shaft proximal portion, in which a portion of the image acquiring lumen is disposed, and a second shaft proximal portion, in which a portion of the guide wire lumen is disposed, the first shaft proximal portion possessing a central axis and an outer periphery, and the second shaft proximal portion possessing a central axis and an outer periphery, the first shaft proximal portion and the second shaft proximal portion being bifurcated so that the central axis of the first shaft proximal portion and the central axis of the second shaft proximal portion are other than parallel and so that a space exists between the outer periphery of the first shaft proximal portion and the outer periphery of the second shaft proximal portion;
a drive shaft rotatably positioned in the image acquiring lumen and axially movable in the image acquiring lumen, the drive shaft possessing a distal end;
a transducer unit configured to acquire images, the transducer unit being fixed to the distal end of the drive shaft so that axial and rotational movement of the drive shaft results in axial and rotational movement respectively of the transducer unit;
a shaft distal portion connected to the distal end of the shaft main body portion, the shaft distal portion possessing a distal end and a proximal end, the shaft distal portion including a lumen that extends from the proximal end of the shaft distal portion to the distal end of the shaft distal portion, the lumen in the shaft distal portion having an open distal end at the distal end of the shaft distal portion and having an open proximal end at the proximal end of the shaft distal portion, the lumen in the shaft distal portion opening to outside the shaft distal portion only at the open distal end of the lumen in the shaft distal portion, the open distal end of the image acquiring lumen and the open distal end of the guide wire lumen both communicating with and opening into the open proximal end of the lumen in the shaft distal portion so that: i) the guide wire positioned in the guide wire lumen in the shaft main body portion is guidable into the lumen in the shaft distal portion and through the open distal end of the lumen in the shaft distal portion while also extending proximally beyond a proximal end of the second shaft proximal portion; and ii) the drive shaft positioned in the image acquiring lumen in the shaft main body portion is guidable into the lumen in the shaft distal portion while also extending proximally beyond a proximal end of the first shaft proximal portion;
a hub that includes a first hub portion interlocked with the first shaft proximal portion and a second hub portion interlocked with the second shaft proximal portion, the first hub portion possessing a central axis and the second hub portion possessing a central axis;
wherein the shaft main body portion possesses an axis line constituting a reference line;
wherein an inclination of the central axis of the first hub portion with respect to the reference line is represented by an angle θ1;
wherein an inclination of the central axis of the second hub portion with respect to the reference line is represented by θ2; and
wherein a relationship of |θ1|>|θ2| is satisfied.

14. The medical device according to claim 13, wherein the hub also includes a hub casing comprised of a distal side fitting portion, a first hub fitting portion and a second hub fitting portion, the distal side fitting portion surrounding an outer peripheral surface of a proximal portion of the shaft main body portion, the first hub fitting portion surrounding an outer peripheral surface of a distal portion of the first hub portion, the second hub fitting portion surrounding an outer peripheral surface of a distal portion of the second hub portion, the distal portion of the first hub portion including a circumferentially extending and outwardly projecting projection positioned in a circumferentially extending recess in an inner peripheral surface of the first hub fitting portion, the distal portion of the second hub portion including a circumferentially extending and outwardly projecting projection positioned in a circumferentially extending recess in an inner peripheral surface of the second hub fitting portion.

15. The medical device according to claim 13, wherein the hub also includes a hub casing comprised of a distal side fitting portion, a first hub fitting portion and a second hub fitting portion, the distal side fitting portion surrounding an outer peripheral surface of a proximal portion of the shaft main body portion, the first hub fitting portion surrounding an outer peripheral surface of a distal portion of the first hub portion, the second hub fitting portion surrounding an outer peripheral surface of a distal portion of the second hub portion, the first and second hub portions each possessing an outer peripheral surface, the first and second hub fitting portions each possessing an inner peripheral surface, further comprising:
  a first interlock structure between the outer peripheral surface of the first hub portion and the inner peripheral surface of the first hub fitting portion to interlock the first hub portion and the first hub fitting portion to one another, the first interlock structure including a circumferentially extending first projection that is positioned in a circumferentially extending first recess, the first projection being provided on one of the inner peripheral surface of the first hub fitting portion and the outer peripheral surface of first hub portion while the first recess is provided on the other of the inner peripheral surface of the first hub fitting portion and the outer peripheral surface of first hub portion; and
  a second interlock structure between the outer peripheral surface of the second hub portion and the inner peripheral surface of the second hub fitting portion to interlock the second hub portion and the second hub fitting portion to one another, the second interlock structure including a circumferentially extending second projection that is positioned in a circumferentially extending second recess, the second projection being provided on one of the inner peripheral surface of the second hub fitting portion and the outer peripheral surface of second hub portion while the second recess is provided on the other of the inner peripheral surface of the second hub fitting portion and the outer peripheral surface of second hub portion.

16. The medical device according to claim 13, wherein the hub also includes a hub casing comprised of a distal side fitting portion, a first hub fitting portion and a second hub fitting portion, the distal side fitting portion surrounding an outer peripheral surface of a proximal portion of the shaft main body portion, the first hub fitting portion surrounding an outer peripheral surface of a distal portion of the first hub portion, the second hub fitting portion surrounding an outer peripheral surface of a distal portion of the second hub portion, the first hub fitting portion possessing an outer peripheral surface and the second hub fitting portion possessing an outer peripheral surface, the hub casing being configured so that the outer peripheral surface of a proximal-most portion of the first hub fitting portion is spaced from the outer peripheral surface of a proximal-most portion of the second hub fitting portion such that a space exists between the outer peripheral surface of the proximal-most portion of the first hub fitting portion and the outer peripheral surface of the proximal-most portion of the second hub fitting portion.

17. An image-acquiring medical device insertable into a body lumen to acquire images inside the body lumen, the image-acquiring medical device comprising:
  a shaft main body portion possessing a distal end at one end of the shaft main body portion and a proximal end at an opposite end of the shaft main body portion, the shaft main body portion including two lumens extending throughout a length of the shaft main body portion from the distal end of the shaft main body portion to the proximal end of the shaft main body portion, the two lumens of the shaft main body portion being separated from one another along the length of the shaft main body portion by a wall, the two lumens in the shaft main body portion comprising an image acquiring lumen and a guide wire lumen, the image acquiring lumen having an open distal end, the guide wire lumen having an open distal end;
  a proximal portion of the shaft main body portion including a first shaft proximal portion, in which a portion of the image acquiring lumen is disposed, and a second shaft proximal portion, in which a portion of the guide wire lumen is disposed, the first shaft proximal portion possessing a central axis and an outer periphery, and the second shaft proximal portion possessing a central axis and an outer periphery, the first shaft proximal portion and the second shaft proximal portion being bifurcated so that the central axis of the first shaft proximal portion and the central axis of the second shaft proximal portion are other than parallel and so that a space exists between the outer periphery of the first shaft proximal portion and the outer periphery of the second shaft proximal portion;
  a shaft distal portion connected to the distal end of the shaft main body portion, the shaft distal portion possessing a distal end and a proximal end, the shaft distal portion including a lumen that extends from the proximal end of the shaft distal portion to the distal end of the shaft distal portion, the lumen in the shaft distal portion having an open distal end at the distal end of the shaft distal portion and having an open proximal end at the proximal end of the shaft distal portion, the lumen in the shaft distal portion opening to outside the shaft distal portion only at the open distal end of the lumen in the shaft distal portion;
  a drive shaft rotatably positioned in the image acquiring lumen and axially movable in the image acquiring lumen, the drive shaft possessing a distal end;
  a transducer unit configured to acquire images, the transducer unit being fixed to the distal end of the drive shaft so that axial and rotational movement of the drive shaft results in axial and rotational movement respectively of the transducer unit, the transducer unit being positioned in the image acquiring lumen and being movable into the lumen in the shaft distal portion;
  the open distal end of the guide wire lumen communicating with and opening into the open proximal end of the lumen in the shaft distal portion;
  a guide wire positioned in the guide wire lumen in the shaft main body portion and in the lumen in the shaft distal portion, the guide wire passing through the open distal end of the lumen in the shaft distal portion while also extending proximally beyond a proximal end of the second shaft proximal portion;
  the open distal end of the image acquiring lumen communicating with and opening into the open proximal end of the lumen in the shaft distal portion so that the drive shaft positioned in the image acquiring lumen in the shaft main body portion is guidable into the lumen in the shaft distal portion while also extending proximally beyond a proximal end of the first shaft proximal portion;
  a hub that includes a first hub portion interlocked with the first shaft proximal portion and a second hub portion interlocked with the second shaft proximal portion, the first hub portion possessing a central axis and the second hub portion possessing a central axis;
  wherein the shaft main body portion possesses an axis line constituting a reference line;
  wherein an inclination of the central axis of the first hub portion with respect to the reference line is represented by an angle $\theta 1$;

wherein an inclination of the central axis of the second hub portion with respect to the reference line is represented by $\theta 2$; and wherein a relationship of $|\theta 1|>|\theta 2|$ is satisfied.

18. The medical device according to claim 17, wherein the hub also includes a hub casing comprised of a distal side fitting portion, a first hub fitting portion and a second hub fitting portion, the distal side fitting portion surrounding an outer peripheral surface of a proximal portion of the shaft main body portion, the first hub fitting portion surrounding an outer peripheral surface of a distal portion of the first hub portion, the second hub fitting portion surrounding an outer peripheral surface of a distal portion of the second hub portion, the first and second hub portions each possessing an outer peripheral surface, the first and second hub fitting portions each possessing an inner peripheral surface, further comprising:

a first interlock structure between the outer peripheral surface of the first hub portion and the inner peripheral surface of the first hub fitting portion to interlock the first hub portion and the first hub fitting portion to one another, the first interlock structure including a circumferentially extending first projection that is positioned in a circumferentially extending first recess, the first projection being provided on one of the inner peripheral surface of the first hub fitting portion and the outer peripheral surface of first hub portion while the first recess is provided on the other of the inner peripheral surface of the first hub fitting portion and the outer peripheral surface of first hub portion; and a second interlock structure between the outer peripheral surface of the second hub portion and the inner peripheral surface of the second hub fitting portion to interlock the second hub portion and the second hub fitting portion to one another, the second interlock structure including a circumferentially extending second projection that is positioned in a circumferentially extending second recess, the second projection being provided on one of the inner peripheral surface of the second hub fitting portion and the outer peripheral surface of second hub portion while the second recess is provided on the other of the inner peripheral surface of the second hub fitting portion and the outer peripheral surface of second hub portion.

19. The medical device according to claim 17, wherein the hub also includes a hub casing comprised of a distal side fitting portion, a first hub fitting portion and a second hub fitting portion, the distal side fitting portion surrounding an outer peripheral surface of a proximal portion of the shaft main body portion, the first hub fitting portion surrounding an outer peripheral surface of a distal portion of the first hub portion, the second hub fitting portion surrounding an outer peripheral surface of a distal portion of the second hub portion, the first hub fitting portion possessing an outer peripheral surface and the second hub fitting portion possessing an outer peripheral surface, the hub casing being configured so that the outer peripheral surface of a proximal-most portion of the first hub fitting portion is spaced from the outer peripheral surface of a proximal-most portion of the second hub fitting portion such that a space exists between the outer peripheral surface of the proximal-most portion of the first hub fitting portion and the outer peripheral surface of the proximal-most portion of the second hub fitting portion.

* * * * *